(12) United States Patent
Xue et al.

(10) Patent No.: US 10,863,919 B2
(45) Date of Patent: Dec. 15, 2020

(54) METHOD AND SYSTEM FOR GRADIENT POWER AMPLIFIER DEBUGGING

(71) Applicant: Shanghai United Imaging Healthcare Co., Ltd., Shanghai (CN)

(72) Inventors: Mingyu Xue, Shanghai (CN); Bin Cao, Shanghai (CN); Xu Chu, Shanghai (CN)

(73) Assignee: Shanghai United Imaging Healthcare Co., Ltd., Shanghai (CN)

( * ) Notice: Subject to any disclaimer, the term of this patent is extended or adjusted under 35 U.S.C. 154(b) by 0 days.

(21) Appl. No.: 16/313,154

(22) PCT Filed: Aug. 12, 2016

(86) PCT No.: PCT/CN2016/094835
§ 371 (c)(1),
(2) Date: Dec. 26, 2018

(87) PCT Pub. No.: WO2018/027893
PCT Pub. Date: Feb. 15, 2018

(65) Prior Publication Data
US 2019/0150783 A1     May 23, 2019

(51) Int. Cl.
*G01V 3/00*     (2006.01)
*A61B 5/055*     (2006.01)
(Continued)

(52) U.S. Cl.
CPC ............ *A61B 5/055* (2013.01); *G01R 33/341* (2013.01); *G01R 33/385* (2013.01); *G01R 33/3852* (2013.01); *G01R 33/543* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 6,138,042 A * 10/2000 Midya .................. H03F 1/0227
                                                            323/222
9,551,767 B2     1/2017 Sabate et al.
(Continued)

FOREIGN PATENT DOCUMENTS

CN     102089671 A     6/2011
CN     102857184 A     1/2013
(Continued)

OTHER PUBLICATIONS

Office Action of Chinese Patent Application No. 201680004737.6 dated Feb. 6, 2020.

*Primary Examiner* — Walter L Lindsay, Jr.
*Assistant Examiner* — Frederick Wenderoth
(74) *Attorney, Agent, or Firm* — Kilpatrick Townsend & Stockton, LLP

(57) ABSTRACT

The present application discloses a gradient power amplifier debugging method and system. The method may comprise initializing a control unit of the gradient power amplifier debugging system; retrieving a characteristic output of the control unit; computing a load inductance parameter L according to the characteristic output; and adjusting the control parameter of the control unit according to the load inductance parameter L. The control unit may comprise a close-loop control sub-unit, or a feedforward control sub-unit. The characteristic output may be representative of the difference between an output signal and an input signal of the gradient power amplifier debugging system. The control parameter may comprise a proportional coefficient, an integral coefficient, or a cutoff frequency of the filter.

20 Claims, 21 Drawing Sheets

(51) Int. Cl.
*G01R 33/385* (2006.01)
*G01R 33/341* (2006.01)
*G01R 33/54* (2006.01)

(58) Field of Classification Search
USPC .......................................................... 324/307
See application file for complete search history.

(56) References Cited

U.S. PATENT DOCUMENTS

| 2011/0074413 | A1 | 3/2011 | Venkatesa | |
|---|---|---|---|---|
| 2011/0133832 | A1 | 6/2011 | Hollander | |
| 2013/0162250 | A1* | 6/2013 | Sabate | G01R 33/3852 |
| | | | | 324/309 |
| 2013/0333477 | A1* | 12/2013 | Kataoka | G01H 9/00 |
| | | | | 73/655 |
| 2014/0266433 | A1* | 9/2014 | Nobbe | H03F 1/30 |
| | | | | 330/151 |

FOREIGN PATENT DOCUMENTS

| CN | 103076580 A | 5/2013 |
|---|---|---|
| CN | 103176150 A | 6/2013 |
| CN | 104237818 A | 12/2014 |

\* cited by examiner

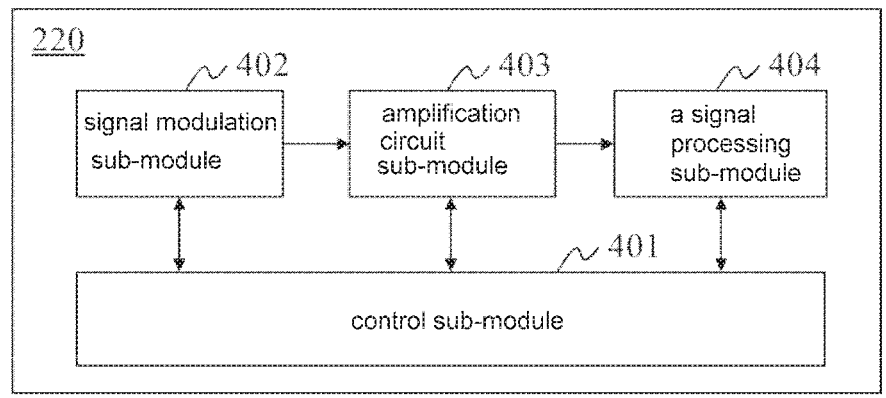
FIG. 4-A
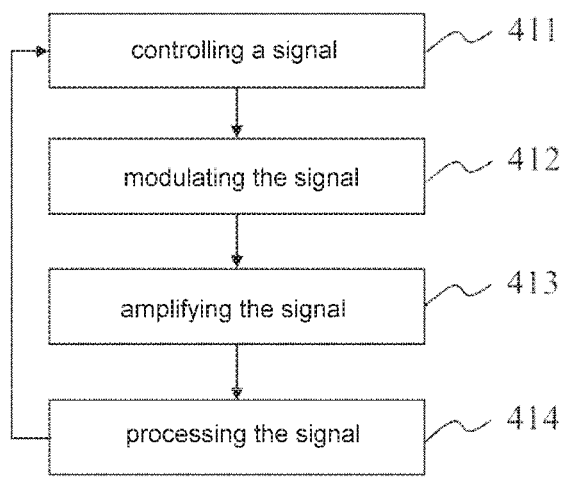
FIG. 4-B

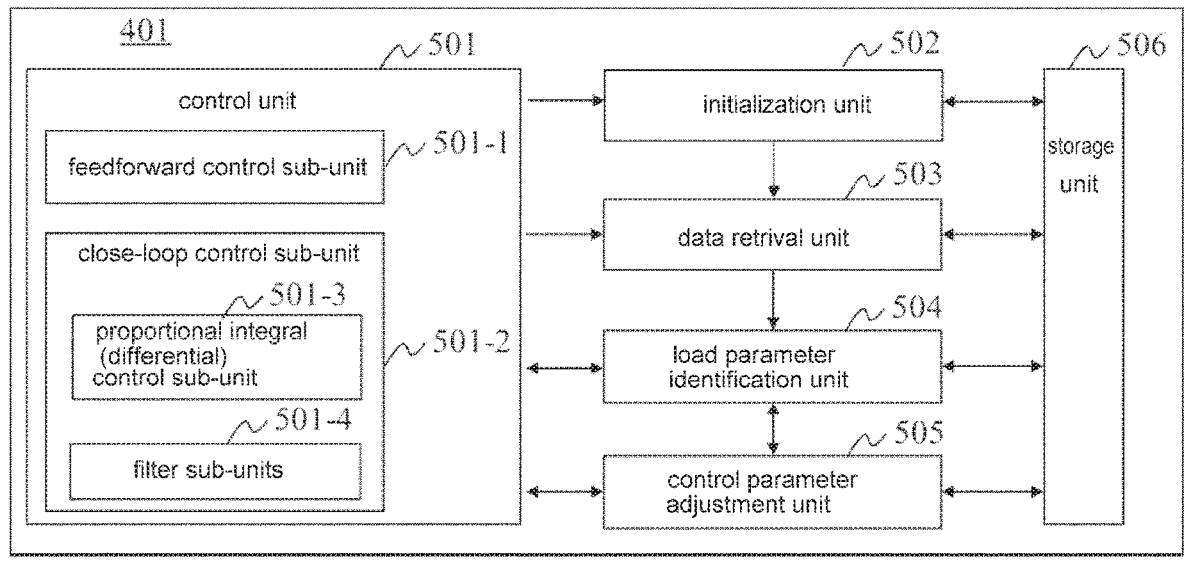
FIG. 5-A
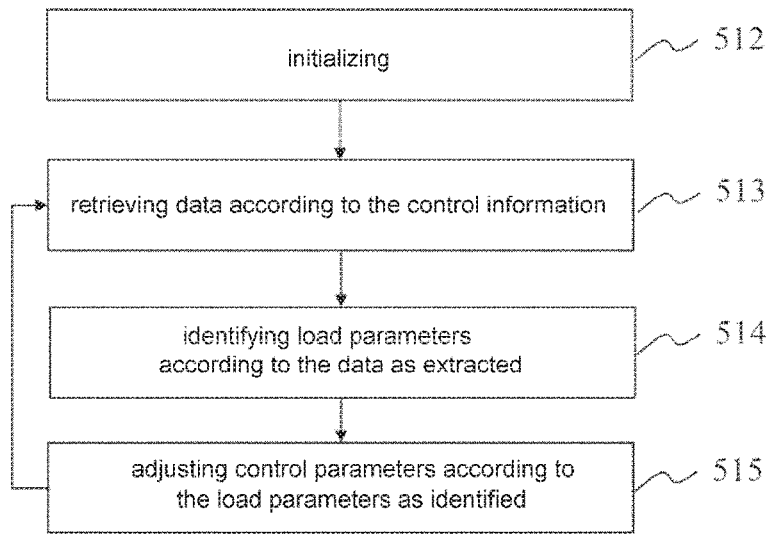
FIG. 5-B

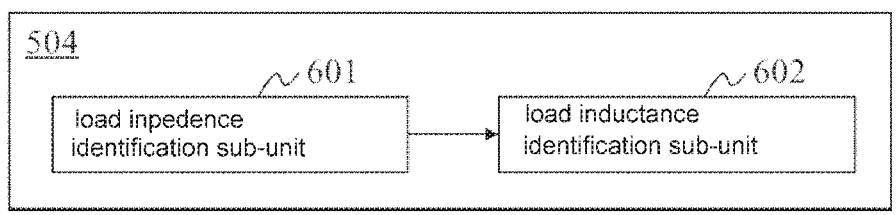
FIG. 6-A
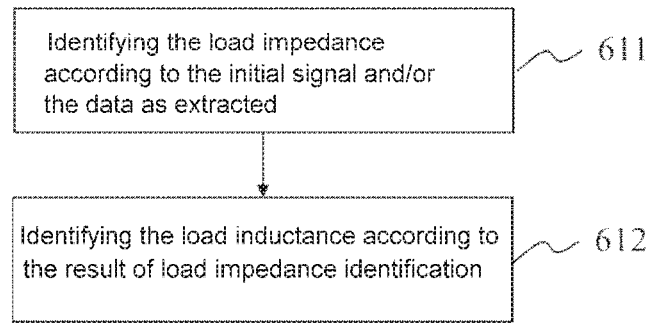
FIG. 6-B

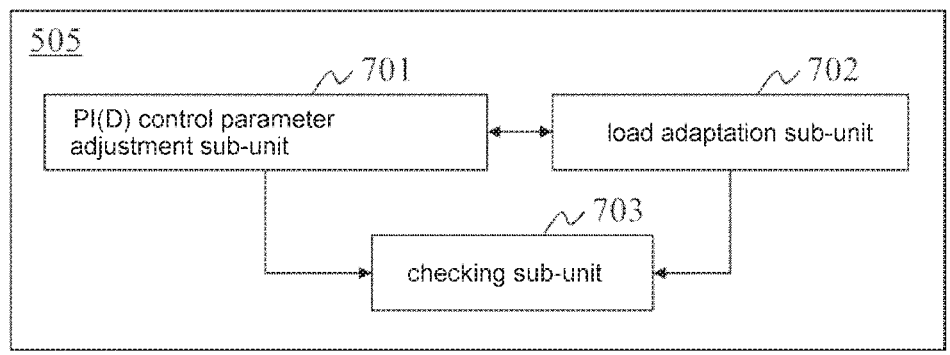
FIG. 7-A
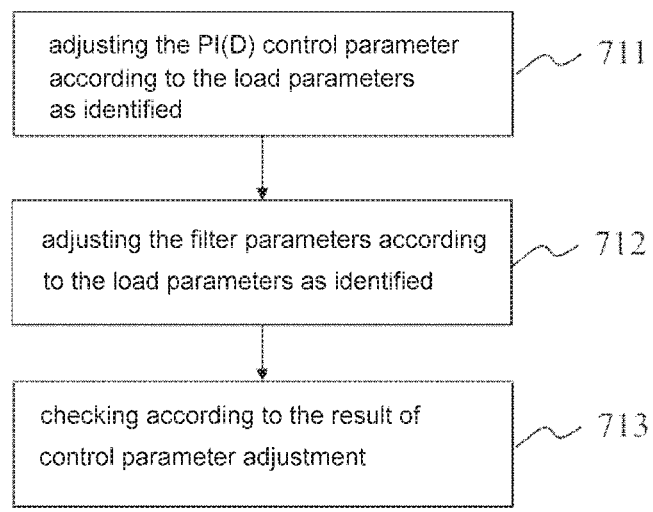
FIG. 7-B

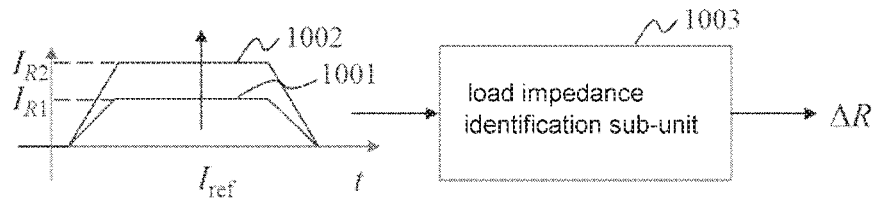
FIG. 10-A
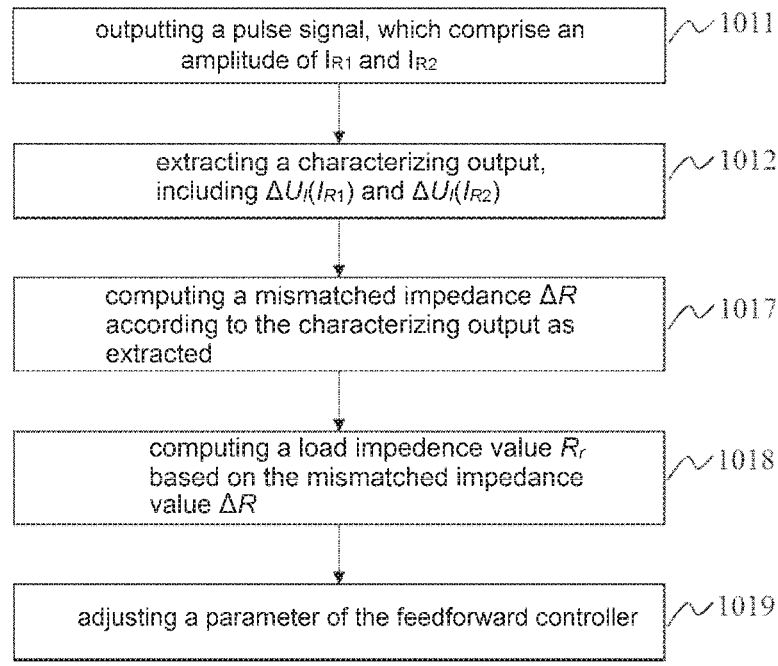
FIG. 10-B

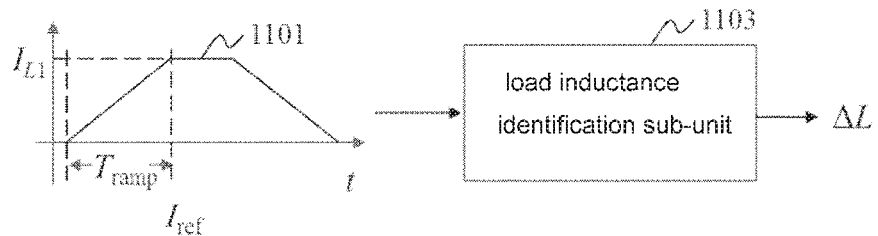
FIG. 11-A
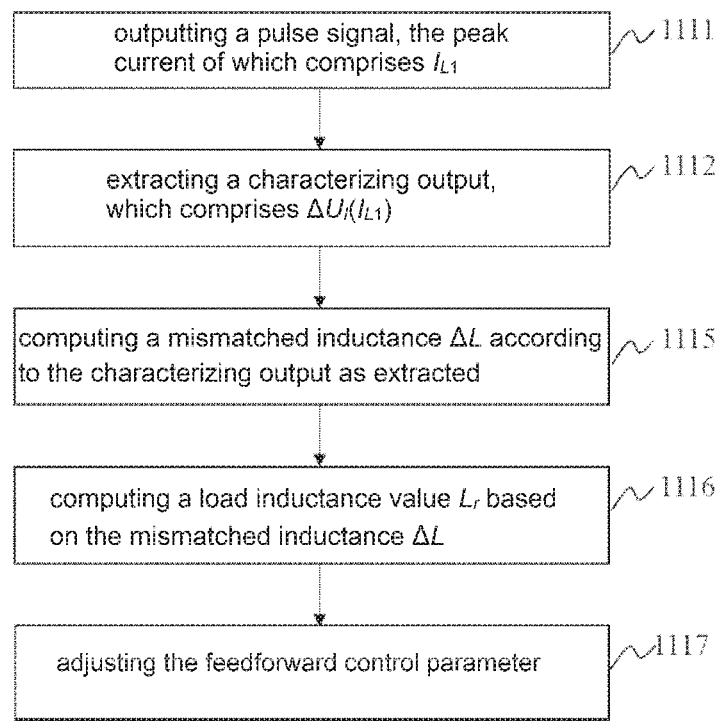
FIG. 11-B

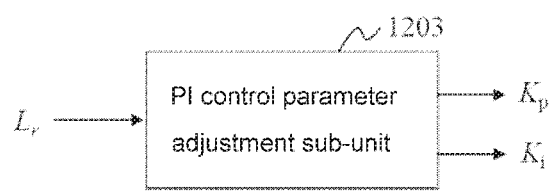
FIG. 12-A
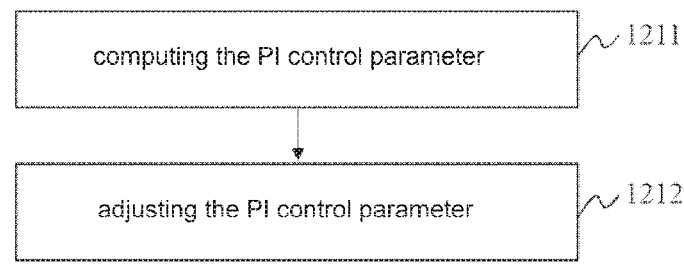
FIG. 12-B

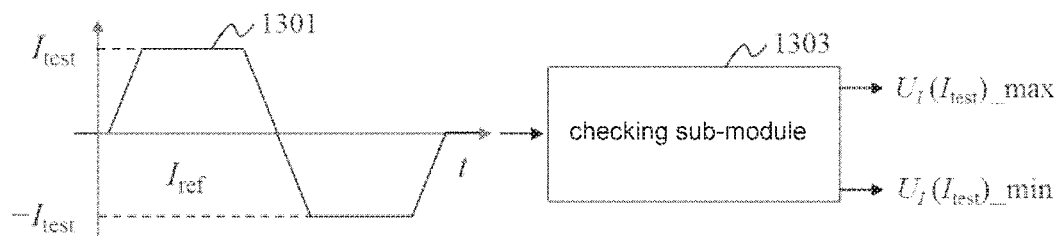
FIG. 13-A
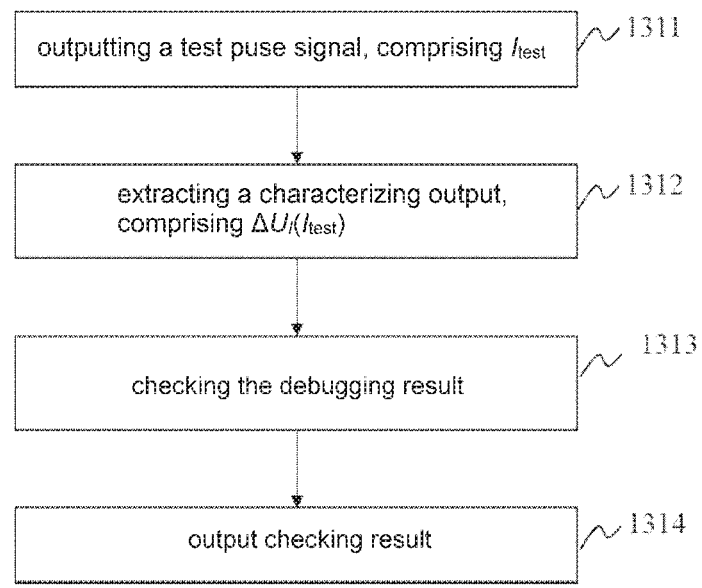
FIG. 13-B

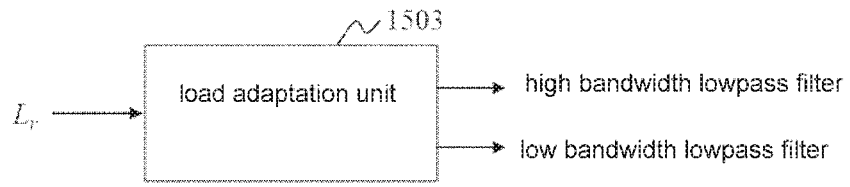
FIG. 15-A
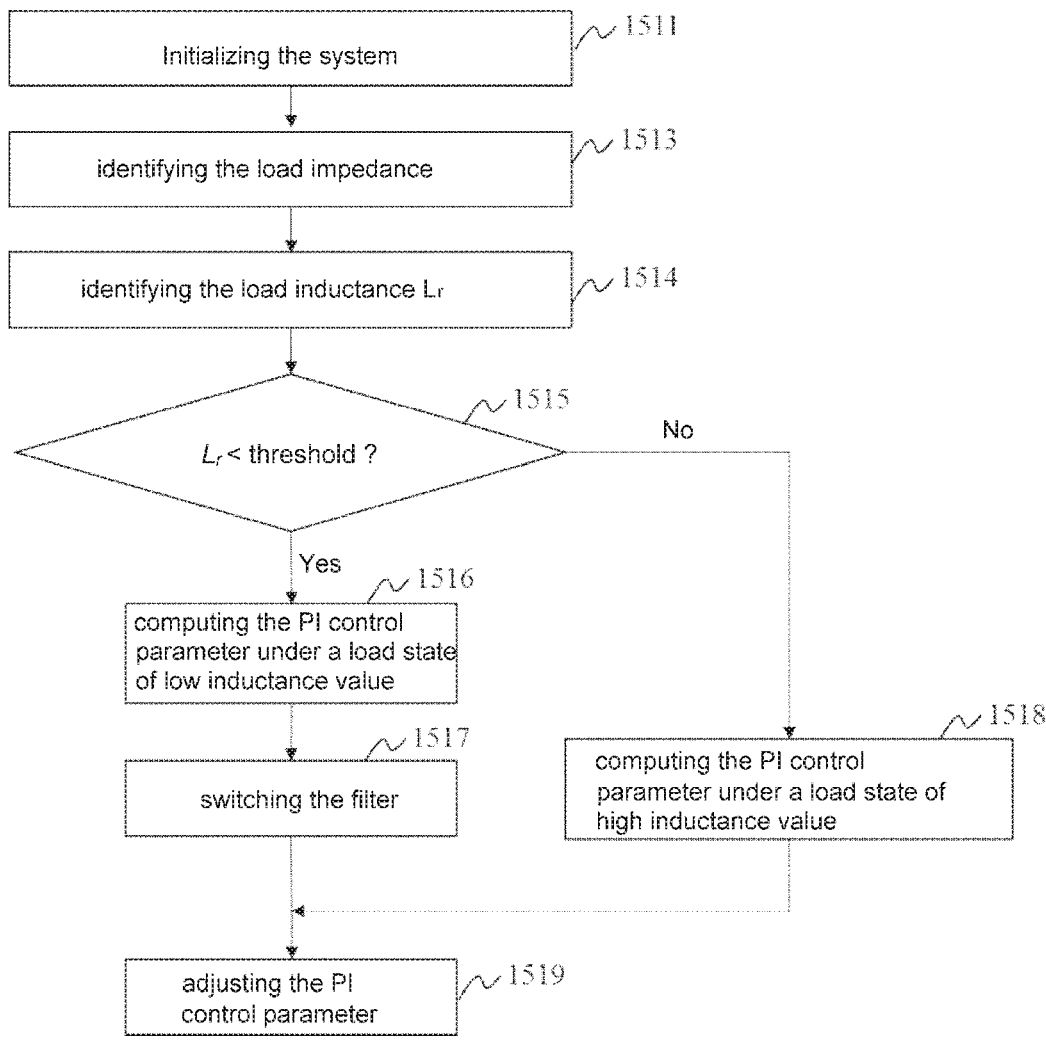
FIG. 15-B

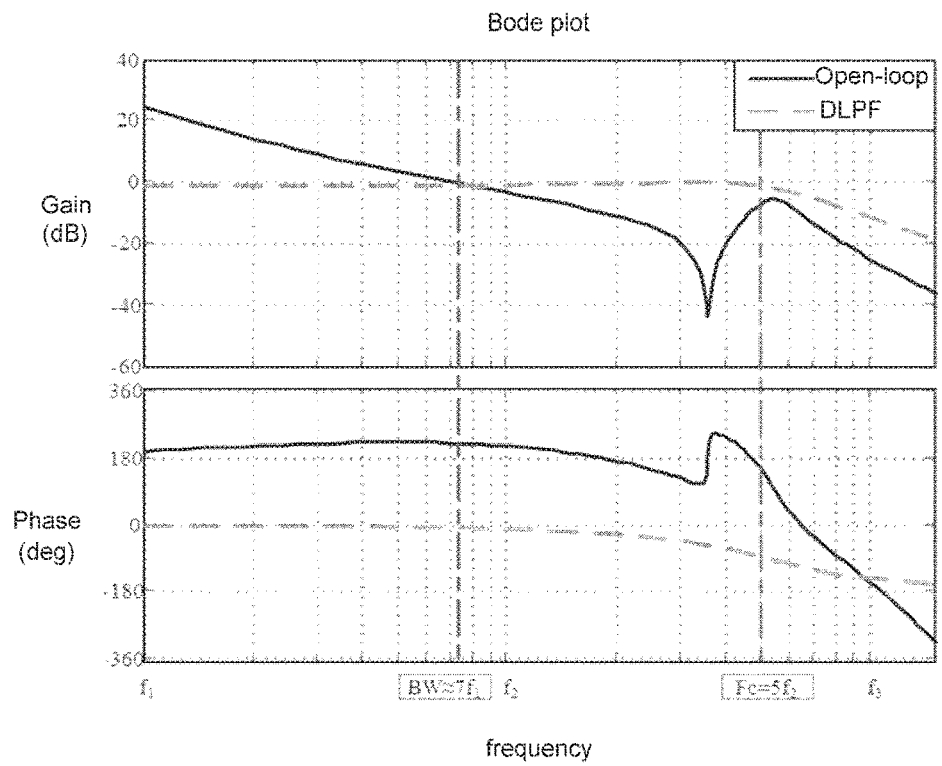
FIG. 19-A
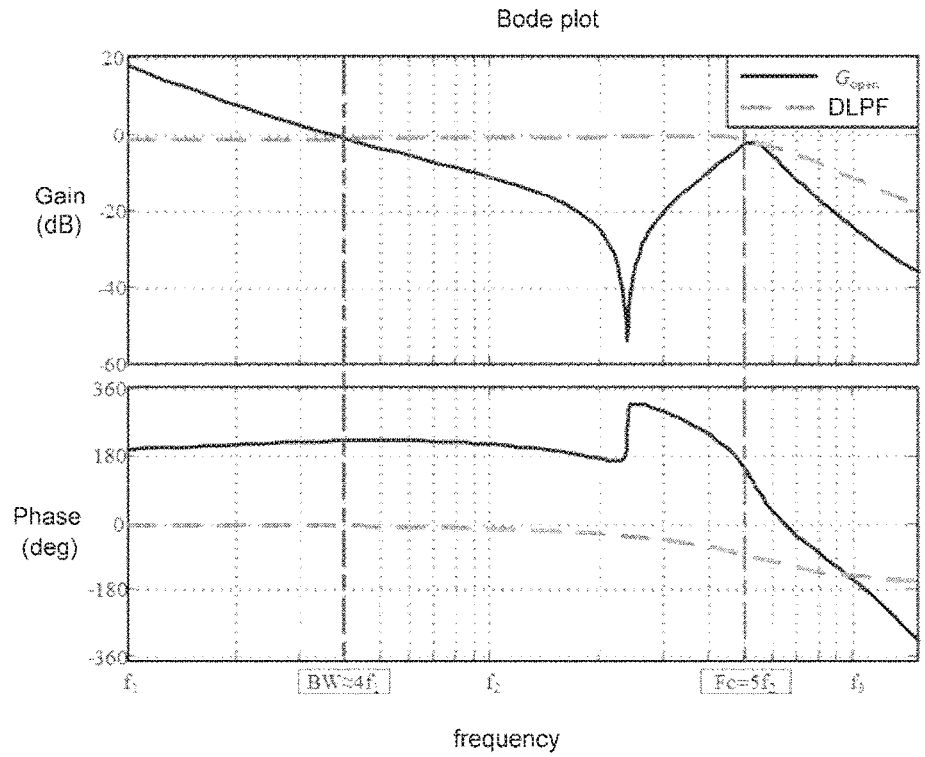
FIG. 19-B

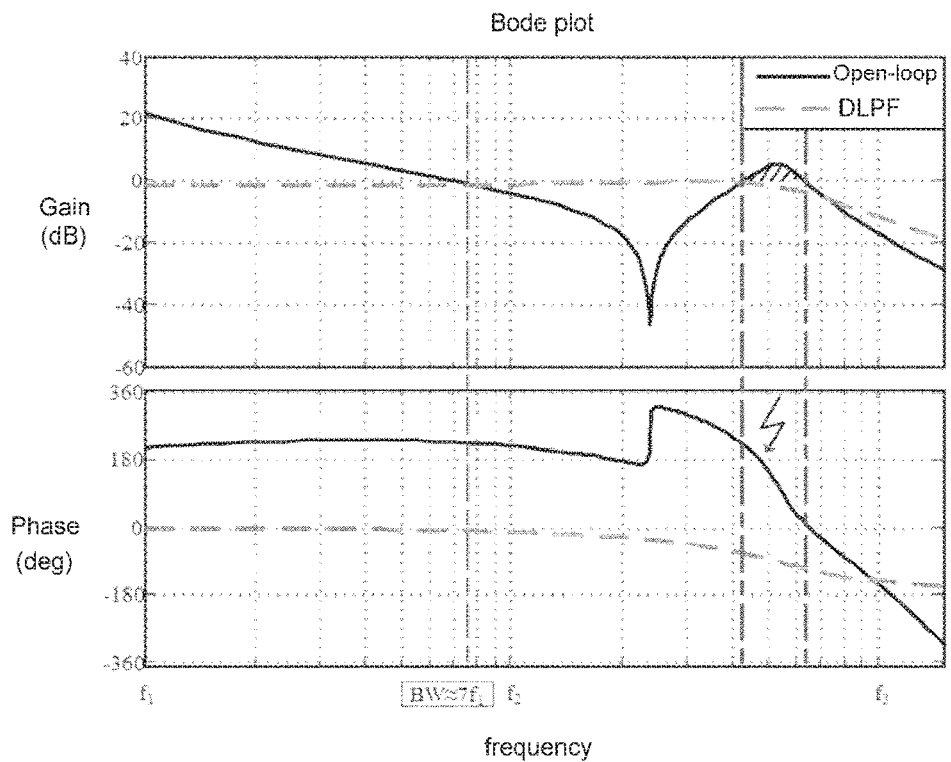
FIG. 19-C
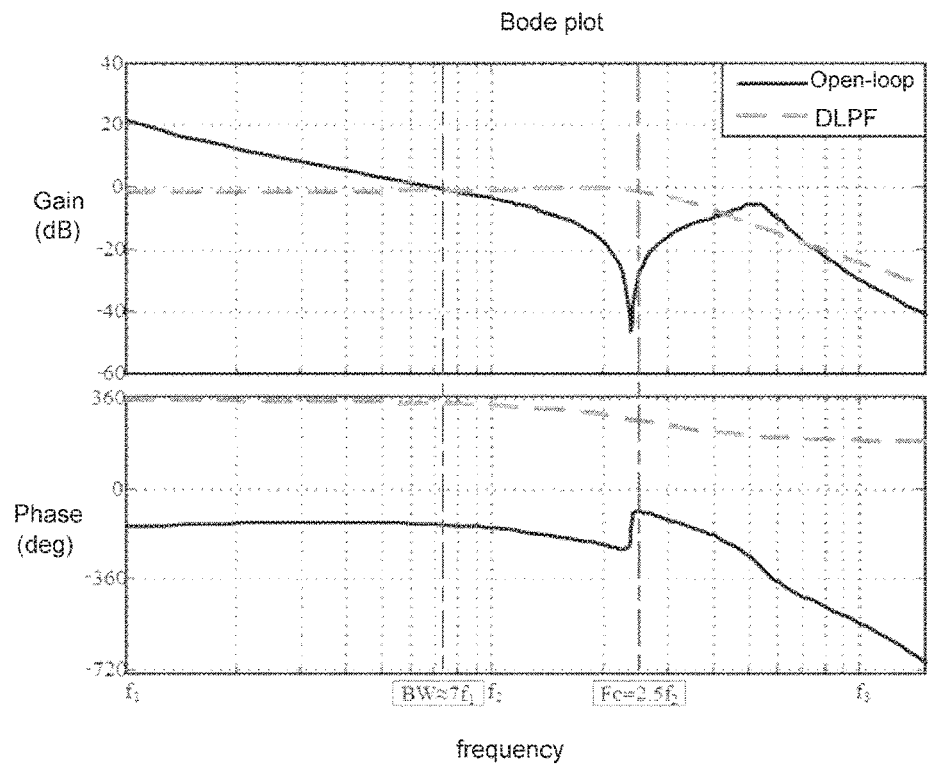
FIG. 20

METHOD AND SYSTEM FOR GRADIENT POWER AMPLIFIER DEBUGGING

CROSS-REFERENCES TO RELATED APPLICATIONS

This application is continuation of International Application No. PCT/CN2016/094835, filed on Aug. 12, 2016, and entitled "METHOD AND SYSTEM FOR GRADIENT POWER AMPLIFIER DEBUGGING", of which is incorporated herein by reference in its entirety.

TECHNICAL FIELD

The present application relates to method and system for gradient power amplifier debugging in an MR debugging system, and in particular, to method and system for gradient power amplifier debugging based on techniques for parameter self-tuning and load adaptation.

BACKGROUND

MR imaging devices are of significance in the field of medical treatment. There are various types of MR imaging devices, which may comprise, for example, Magnetic Resonance Imaging (MRI), Magnetic Resonance Angiography (MRA), SPECT-MR, DSA-MR, PET-MR, TMS-MR, US-MR, etc., or any combination thereof. When an MR device performs imaging, it needs a gradient magnetic field for spatial encoding, which may be induced by a driven current applied to a gradient coil by a gradient power amplifier. The gradient power amplifier may provide the MR imaging device with a fast variable gradient magnetic field with certain linearity, thereby achieving spatial positioning and encoding of the imaging voxels. The performance of the gradient magnetic field provided by the gradient power amplifier may affect the imaging quality and rate of the MR device. In the MR imaging device, in order to guarantee proper operation of the MR device, to improve the performance of the gradient magnetic field, to increase precision of the output current of the gradient power amplifier, and to adapt the gradient power amplifier to a gradient coil having a wider range of inductance, the gradient power amplifier needs to be debugged in the stages of setup debugging, use, maintenance, or fixing of the MR device.

SUMMARY

According to an aspect of the present disclosure, a method for debugging a gradient power amplifier debugging is provided. The method for debugging a gradient power amplifier debugging may include: initializing a control unit in the gradient power amplifier debugging system; retrieving a characteristic output of the control unit; computing a load inductance parameter L according to the characteristic output; and adjusting a control parameter of the control unit according to the load inductance parameter L. The characteristic output may represent a difference between an input signal and an output signal of the gradient power amplifier debugging system.

In another aspect of the present disclosure, a system for debugging a gradient power amplifier debugging is provided. The gradient power amplifier debugging system may include a control unit, an initialization unit, a data retrieval unit, a load parameter identification unit, and a control parameter adjustment unit. The control unit may include a close-loop control sub-unit and a feedforward control sub-unit. The initialization unit may be configured to initialize the control unit. The data retrieval unit may be configured to retrieve a characteristic output of the control unit. The load parameter identification unit may be configured to compute a load inductance parameter L according to the characteristic output. The control parameter adjustment unit may be configured to adjusting a control parameter of the control unit according to the load inductance parameter L. The characteristic output may represent a difference between an input signal and an output signal of the gradient power amplifier debugging system.

According to some embodiments of this application, the control unit comprises: a close-loop control sub-unit and a feedforward control sub-unit. The close-loop control sub-unit may comprise a proportional integral (PI) controller or a proportional integral differential (PID) controller, etc. The feedforward control sub-unit may comprise a load inductance model, the load inductance model comprising the load inductance parameter L.

According to some embodiments of this application, the initializing may include initializing the load inductance parameter L.

According to some embodiments of this application, the characteristic output may comprise an integral output of the PI controller, a proportional output, or a differential output of the PID controller.

According to some embodiments of this application, the feedforward control sub-unit may comprise a load impedance model, the load impedance model may comprise a load impedance parameter R.

According to some embodiments of this application, the initializing may comprise initializing the load impedance parameter R.

According to some embodiments of this application, retrieving the characteristic output may comprise: retrieving a first characteristic output of the control unit when the control unit outputs a pulse signal of a first amplitude; and retrieving a second characteristic output of the control unit when the control unit outputs a pulse signal of a second amplitude.

According to some embodiments of this application, the pulse signal of the first amplitude and the pulse signal of the second amplitude may be mono-polarity pulses.

According to some embodiments of this application, the first amplitude and the second amplitude may be not lower than a first threshold, the first threshold may be such that a difference between the first characteristic output and the second characteristic output is only dependent on the load impedance parameter R of the load impedance model.

According to some embodiments of this application, computing the load inductance parameter L may comprise: computing a mismatched impedance $\Delta R$ between the load impedance parameter R of the load impedance model and a real load impedance R' of the gradient power amplifier debugging system, according to the first characteristic output and the second characteristic output; and adjusting the load impedance parameter of the load impedance model to $\Delta R + R$, according to the mismatched impedance $\Delta R$ and the load impedance parameter R of the load impedance model; retrieving a third characteristic output of the control unit when the control unit outputs a pulse signal of a third amplitude, according to the load impedance model of the load impedance parameter $\Delta R + R$, wherein the pulse signal of the third amplitude is a mono-polarity pulse, the pulse signal of the third amplitude comprises a rising time of $T_{ramp}$, which is not lower than a second threshold, such that a characteristic output in the rising time $T_{ramp}$ is only dependent on the load inductance parameter L of the load inductance model; computing a mismatched inductance ΔL between the load inductance parameter L of the load inductance model and a real load inductance L' of the gradient power amplifier debugging system, according to the third characteristic output and the rising time $T_{ramp}$; and adjusting the load inductance parameter of the load inductance model to ΔL+L, according to the mismatched inductance ΔL and the load inductance parameter L of the load inductance model.

According to some embodiments of this application, retrieving the characteristic output may comprise: retrieving a fourth characteristic output of the control unit when the control unit outputs a pulse signal of a fourth amplitude.

According to some embodiments of this application, the pulse signal of the fourth amplitude may comprise a mono-polarity pulse, and the pulse signal of the fourth amplitude may comprise a rising time of $T_{ramp}'$.

According to some embodiments of this application, the rising time $T_{ramp}'$ may be not lower than a second threshold, such that a characteristic output in the rising time $T_{ramp}'$ is only dependent on the load inductance parameter L of the load inductance model.

According to some embodiments of this application, computing the load inductance parameter L may comprise: computing a mismatched inductance ΔL between the load inductance parameter L of the load inductance model and a real load inductance L' of the gradient power amplifier debugging system, according to the fourth characteristic output and the rising time $T_{ramp}'$; and adjusting the load inductance parameter of the load inductance model to ΔL+L, according to the mismatched inductance ΔL and the load inductance parameter L of the load inductance model.

According to some embodiments of this application, the control parameter may comprise a proportional coefficient Kp of the PI controller.

According to some embodiments of this application, the initializing may comprise initializing the proportional coefficient $K_p$.

According to some embodiments of this application, adjusting the control parameter of the control unit may comprise adjusting a value of the proportional coefficient $K_p$ to αL, wherein α is a constant.

According to some embodiments of this application, the control parameter may further comprise an integral coefficient $K_i$ of the PI controller.

According to some embodiments of this application, the initializing may comprise initializing the integral coefficient $K_i$.

According to some embodiments of this application, adjusting the control parameter of the control unit may further comprise adjusting a value of the integral coefficient $K_i$ to βL, wherein β is a constant.

According to some embodiments of this application, the control unit may further comprise a first digital low-pass filter.

According to some embodiments of this application, the initializing may comprise initializing a cutoff frequency of the first digital low-pass filter to an initial cutoff frequency According to some embodiments of this application, the adjusting the control parameter of the control unit may comprise: comparing the load inductance parameter L to a threshold; adjusting the proportional coefficient $K_p$ to $α_1L$, if the load inductance parameter L is lower than the threshold, wherein al is a constant; and adjusting the proportional coefficient $K_p$ to $α_2L$, if the load inductance parameter L is higher than the threshold, wherein $α_2$ is a constant.

According to some embodiments of this application, the adjusting the control parameter of the control unit may comprise: comparing the load inductance parameter L to a threshold; adjusting the integral coefficient Ki to $β_1L$, if the load inductance parameter L is lower than the threshold, wherein $β_1$ is a constant; and adjusting the integral coefficient Ki to $β_2L$, if the load inductance parameter L is higher than the threshold, wherein $β_2$ is a constant.

According to some embodiments of this application, the adjusting the control parameter of the control unit may comprise: comparing the load inductance parameter L to a threshold; adjusting the cutoff frequency of the first digital low-pass filter to a first cutoff frequency, if the load inductance parameter L is lower than the threshold; and adjusting the cutoff frequency of the first digital low-pass filter to a second cutoff frequency, if the load inductance parameter L is higher than the threshold.

According to some embodiments of this application, the first cutoff frequency or the second cutoff frequency may be equal to the initial cutoff frequency.

According to some embodiments of this application, the control unit may further comprise a second digital low-pass filter, and adjusting the control parameter of the control unit may comprise: comparing the load inductance parameter L to a threshold; and switching between the first digital low-pass filter and the second digital low-pass filter according to the result of the comparison.

According to some embodiments of this application, the system for debugging a gradient power amplifier debugging may further comprise executable instructions which, when executed by at least one processor, causes the at least one processor to implement a method. The method may comprise: initializing the load inductance parameter L, the load impedance parameter R, the proportional coefficient $K_p$, and the integral coefficient K; retrieving a first characteristic output of the control unit when the control unit outputs a pulse signal of a first amplitude, wherein the pulse of the first amplitude is a mono-polarity pulse; and retrieving a second characteristic output of the control unit when the control unit outputs a pulse signal of a second amplitude, wherein the pulse of the second amplitude is a mono-polarity pulse, the first amplitude and the second amplitude are not lower than a first threshold, the first threshold may be such that a difference between the first characteristic output and the second characteristic output is only dependent on the load impedance parameter R of the load impedance model; computing a mismatched impedance ΔR between the load impedance parameter R of the load impedance model and a real load impedance R' of the gradient power amplifier debugging system, according to the first characteristic output and the second characteristic output; adjusting the load impedance parameter of the load impedance model to ΔR+R, according to the mismatched impedance ΔR and the load impedance parameter R of the load impedance model; retrieving a third characteristic output of the control unit when the control unit outputs a pulse signal of a third amplitude, according to the load impedance model of the load impedance parameter ΔR+R, wherein the pulse signal of the third amplitude is a mono-polarity pulse, the pulse signal of the third amplitude comprises a rising time of $T_{ramp}$, which is not lower than a second threshold, such that a characteristic output in the rising time $T_{ramp}$ is only dependent on the load inductance parameter L of the load inductance model; computing a mismatched inductance ΔL between the load inductance parameter L of the load inductance model and a real load inductance L' of the gradient power amplifier debugging system, according to the third characteristic output and the rising time $T_{ramp}$; and adjusting the load inductance parameter of the load inductance model to ΔL+L, according to the mismatched inductance ΔL and the load inductance parameter L of the load inductance model.

According to some embodiments of the present application, the method may further comprise: adjusting the value of the proportional coefficient $K_p$ to α(ΔL+L), where α may be a constant; adjusting the value of the integral coefficient Ki to β(ΔL+L), where β may be a constant.

According to some embodiments of the present application, the method may further include: comparing the load inductance parameter (ΔL+L) with a threshold value; adjusting the proportional coefficient $K_p$ to be $α_1L$, adjusting the integral coefficient Ki to be $β_1L$ if the load inductance parameter (ΔL+L) is below a threshold value, and adjusting the cut-off frequency of the digital low pass as the first cut-off frequency; if the load inductance parameter (ΔL+L) is higher than the threshold value, adjusting the proportional coefficient $K_p$ to $α_2L$, adjusting the integral coefficient $K_i$ to $β_2L$, and adjusting the cut-off frequency of the digital low pass filter to the second cut-off frequency.

Some of the additional features of this application can be explained in the following description. Some of the additional features of this application are apparent to those skilled in the art by examining the following description and the corresponding drawings or by understanding the production or operation of the implementation. The features of this disclosure may be realized and achieved through the practice or use of various aspects of methods, means and combinations of embodiments described below.

DESCRIPTION OF DRAWINGS

The drawings described herein are used to provide a further understanding of this application and form part of this application. The illustrative embodiments of this application and their illustrations for the interpretation of this application do not constitute a limitation on this application. In each diagram, the same label indicates the same parts.

FIG. 4-A is a schematic diagram of an amplified signal generation module shown in some embodiments of the present application;

FIG. 4-B is an exemplary flowchart for generating amplified signals shown in some embodiments of the present application;

The diagram 5-A is a schematic diagram of the control sub module shown in some embodiments of this application.

The diagram 5-B is an example flow chart of signal control shown in some embodiments of this application.

Figure 8:
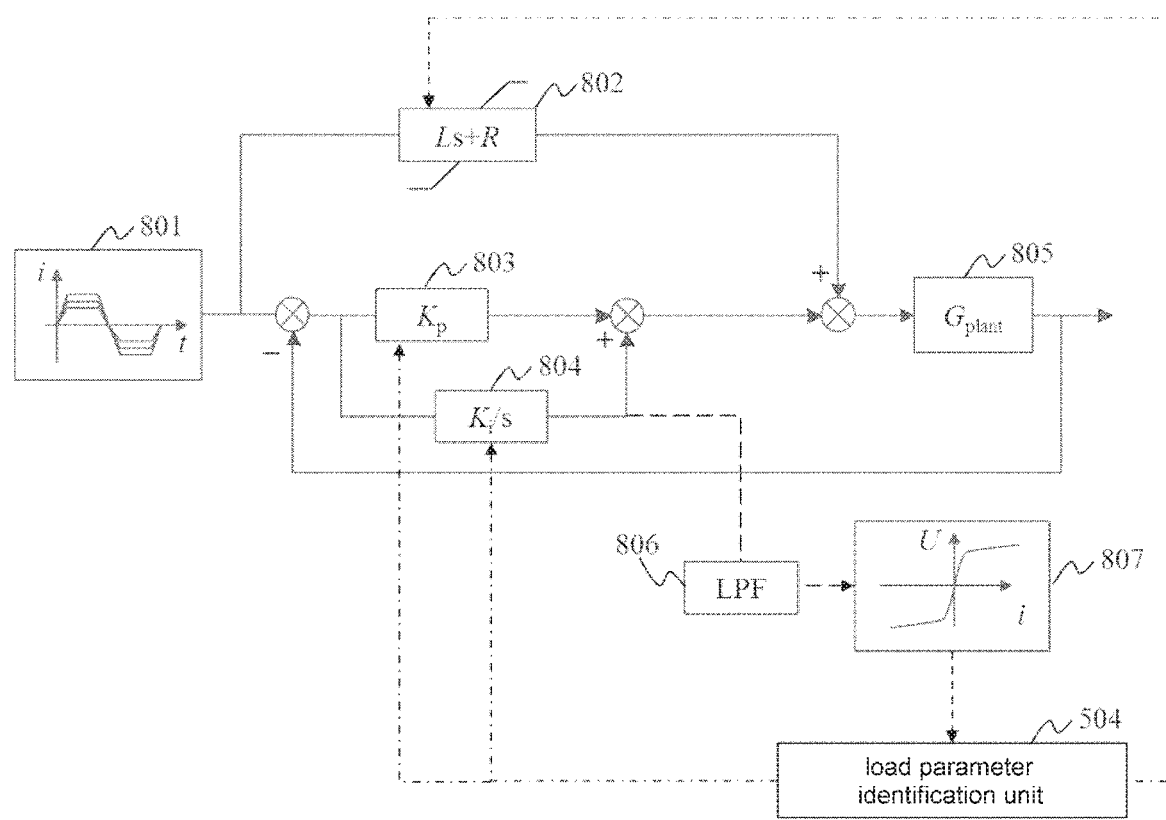
Figure 9:
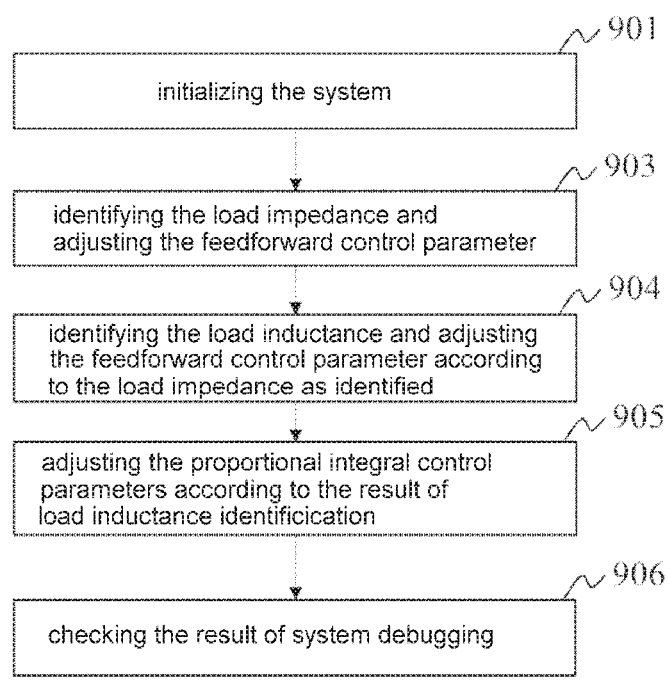

FIG. 6-A is a schematic diagram of a load parameter identification unit shown in some embodiments of the present application;

FIG. 6-B is an exemplary flow chart for load parameter identification shown in some embodiments of the present application;

FIG. 7-A is a schematic diagram of a control parameter adjustment unit shown in some embodiments of the present application;

FIG. 7-B is an example flowchart of control parameter adjustment shown in some embodiments of the present application;

FIG. 8 is a schematic diagram of one embodiment of the control sub-module shown in some embodiments of the present application;

FIG. 9 is a schematic flowchart of the parameter self-tuning process of the gradient power amplifier debugging system showned in some embodiments of the present application.

FIG. 10-A is a schematic diagram of a load impedance identification subunit shown in some embodiments of the present application;

FIG. 10-B is an exemplary flow chart for load impedance identification shown in some embodiments of the present application;

FIG. 11-A is a schematic diagram of a load inductance identification subunit shown in some embodiments of the present application;

FIG. 11-B is an exemplary flow chart for load inductance identification shown in some embodiments of the present application;

FIG. 12-A is a schematic diagram of a PI control parameter adjustment subunit shown in some embodiments of the present application;

FIG. 12-B is an example flowchart of PI control parameter adjustment shown in some embodiments of the present application;

The diagram 13-A is a schematic diagram of the calibration sub unit shown in some embodiments of this application.

Figure 14:
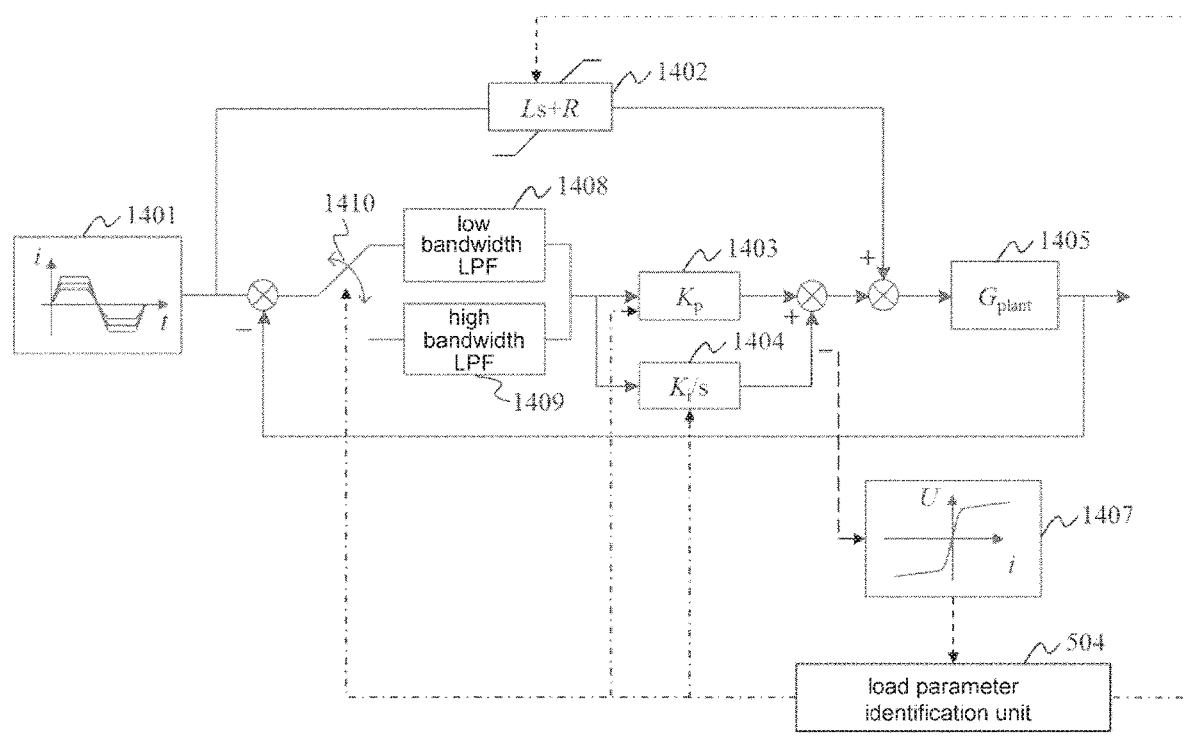
Figure 16:
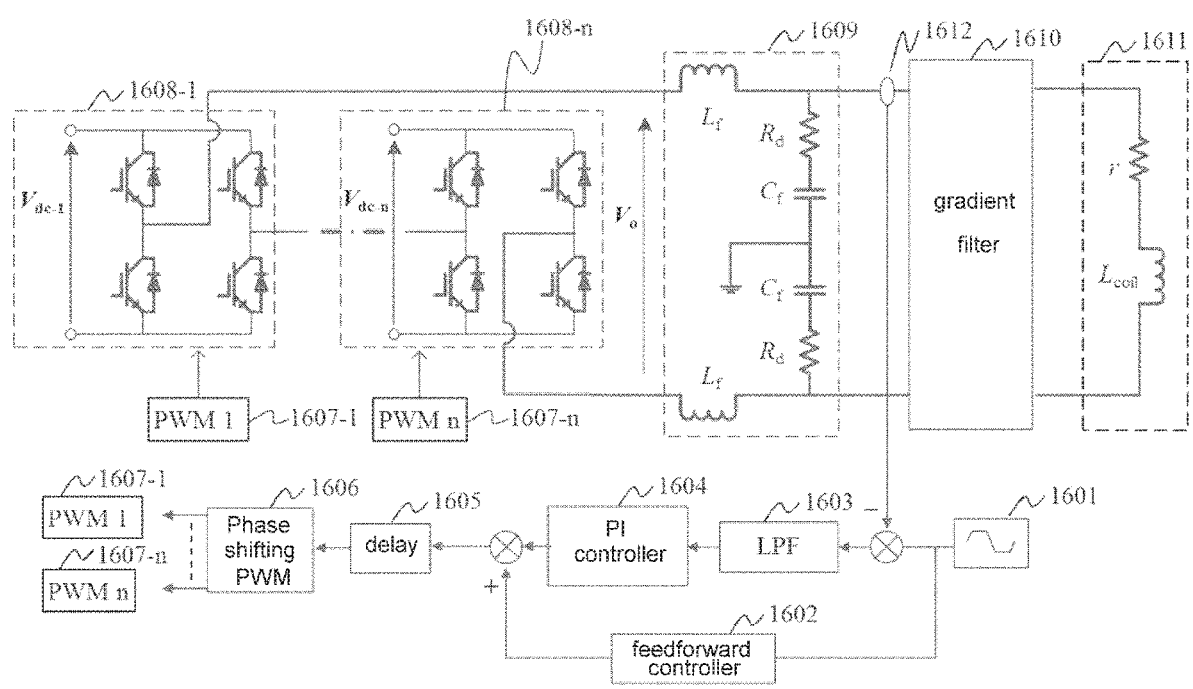
Figure 17:
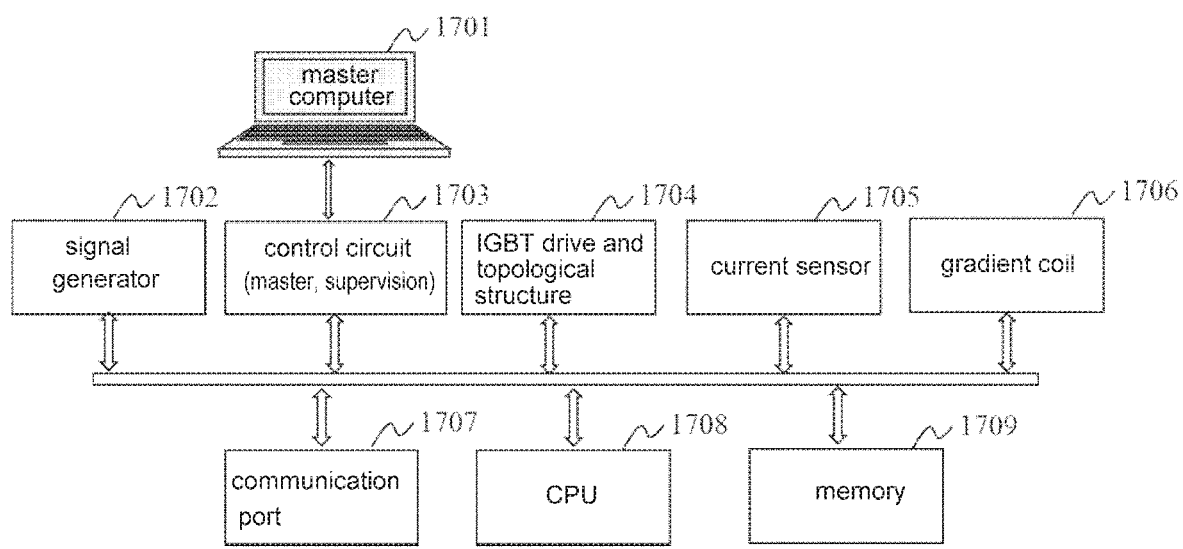

FIG. 13-B is an example flowchart of parameter self-tuning calibration shown in some embodiments of the present application;

FIG. 14 is a schematic diagram of another embodiment of the control sub-module shown in some embodiments of the present application;

FIG. 15-A is a schematic diagram of a load adaptive subunit shown in some embodiments of the present application;

FIG. 15-B is an exemplary flow chart of load adaptation illustrated in accordance with some embodiments of the present application;

FIG. 16 is a schematic diagram of one embodiment of the gradient power amplifier debugging system shown in some embodiments of the present application;

FIG. 17 is a schematic diagram of the hardware configuration of the gradient power amplifier debugging system shown in some embodiments of the present application.

Figure 18:
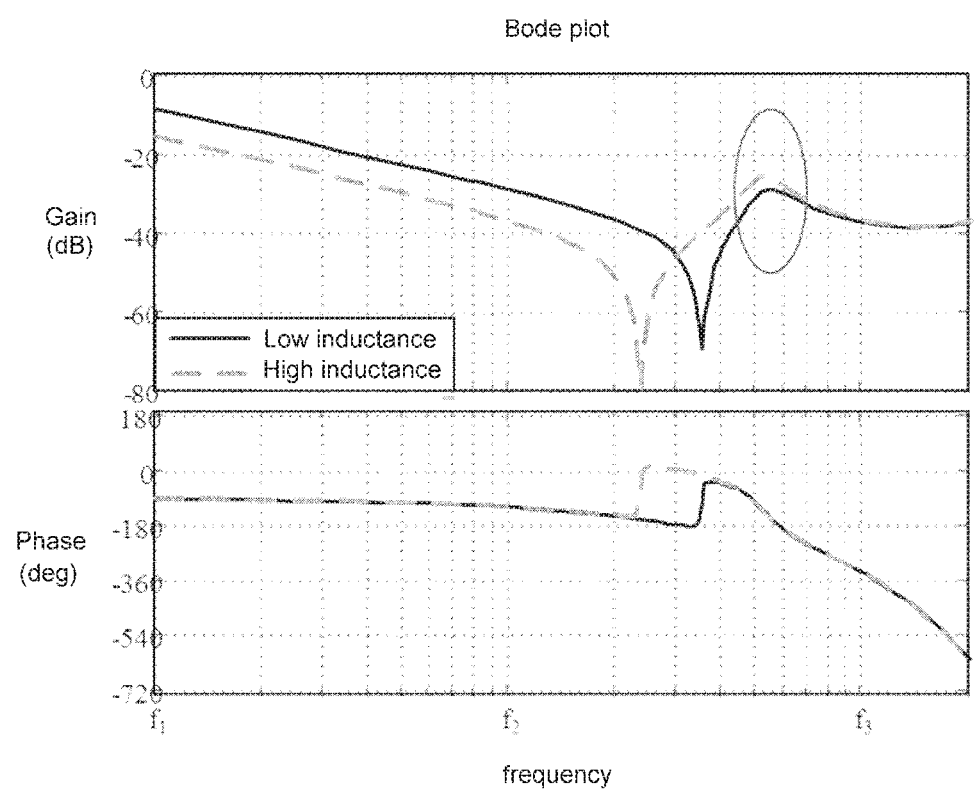

FIG. 18 is a schematic diagram of the frequency response of the output voltage to the output current when the gradient power amplifier is connected to a gradient coil of different inductance values, as shown in some embodiments of the present application;

FIG. 19-A is a schematic diagram of the open-loop frequency response of the system and the corresponding low-pass filter characteristics when a gradient power amplifier is connected to a gradient coil with a low inductance, as shown in some embodiments of the present application.

FIG. 19-B is a schematic diagram of the open-loop frequency response and low-pass filter characteristics of a gradient power amplifier connected to a gradient coil with a high inductance when the system adopts the corresponding control parameters of a gradient coil with a low inductance, as shown in some embodiments of the present application.

FIG. 19-C is a schematic diagram of an open-loop frequency response corresponding to a direct increase in PI parameters when a gradient power amplifier is connected to a gradient coil with a high inductance, as shown in some embodiments of the present application.

Figure 21:
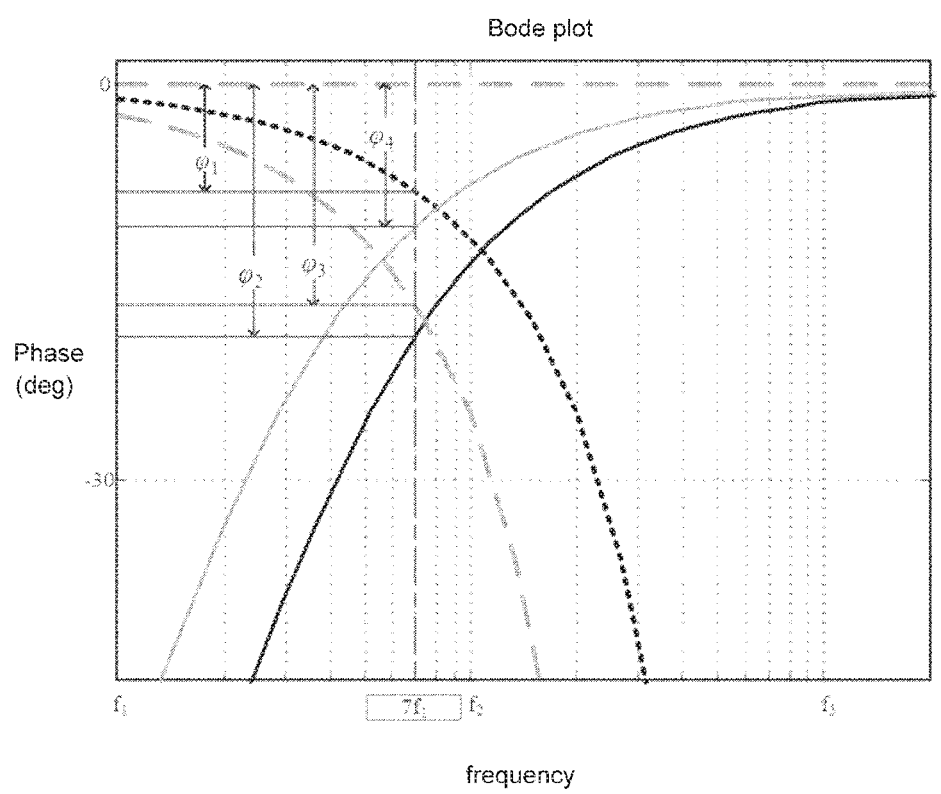

FIG. 20 is a schematic diagram of the open-loop frequency response of a low-pass filter when a gradient power amplifier is connected to a gradient coil with a high inductance while increasing the PI parameter and adjusting the cut-off frequency of the low-pass filter, as shown in some embodiments of the present application; and FIG. 21 is the phase characteristics of the PI controller and the low-pass filter at approximate bandwidth when the gradient power amplifier is connected to a gradient coil of different inductance values according to some embodiments of the present application.

DETAILED DESCRIPTION

To illustrate more clearly the technical scheme of the embodiments of this application, a brief description of the drawings to be used in the description of the embodiments will be given below. Obviously, the drawings described below are only some examples or embodiments of the present application, and for those of ordinary skill in the art, the present application may be applied to other similar scenarios without creative effort. The same label in the diagram represents the same structure or operation unless it is apparent from the language environment or otherwise specified.

As indicated in this application and claim, the words "one", "one", "one", "one" and/or "the" do not refer specifically to singular numbers, but may also include plural numbers, unless the upper and lower civilizations clearly indicate exceptions. Generally speaking, the terms "include" and "include" only indicate the inclusion of clearly identified steps and elements that do not constitute an exclusive list, and methods or devices may contain other steps or elements.

Although various references are made to certain modules in the system according to the embodiment of the present application, any number of different modules may be used and run on a gradient power amplifier debugging system. The modules are illustrative only, and different aspects of the systems and methods may use different modules.

A flowchart is used in this application to illustrate the operational steps performed by the system according to the embodiment of the application. It should be understood that the steps do not necessarily follow the order accurately. Conversely, steps can be handled in reverse order or at the same time. At the same time, other steps can be added to or removed from these processes.

The implementation of this application can be applied to the debugging of gradient power amplifiers of different devices. Different devices may include MRI device, PET-MRI device, SPECT-MRI device, and so on. Debugging of equipment can include debugging of MRI equipment during installation stage, debugging in daily use process, debugging in equipment maintenance and maintenance process, etc. It should be understood that the application scenarios of the systems and methods of the present application are only some examples or embodiments of the present application, and that, for those of ordinary skill in the art, the present application may be applied to other similar scenarios without creative effort. For example, the debug system of gradient power amplifier other than MRI.

Figure 1:
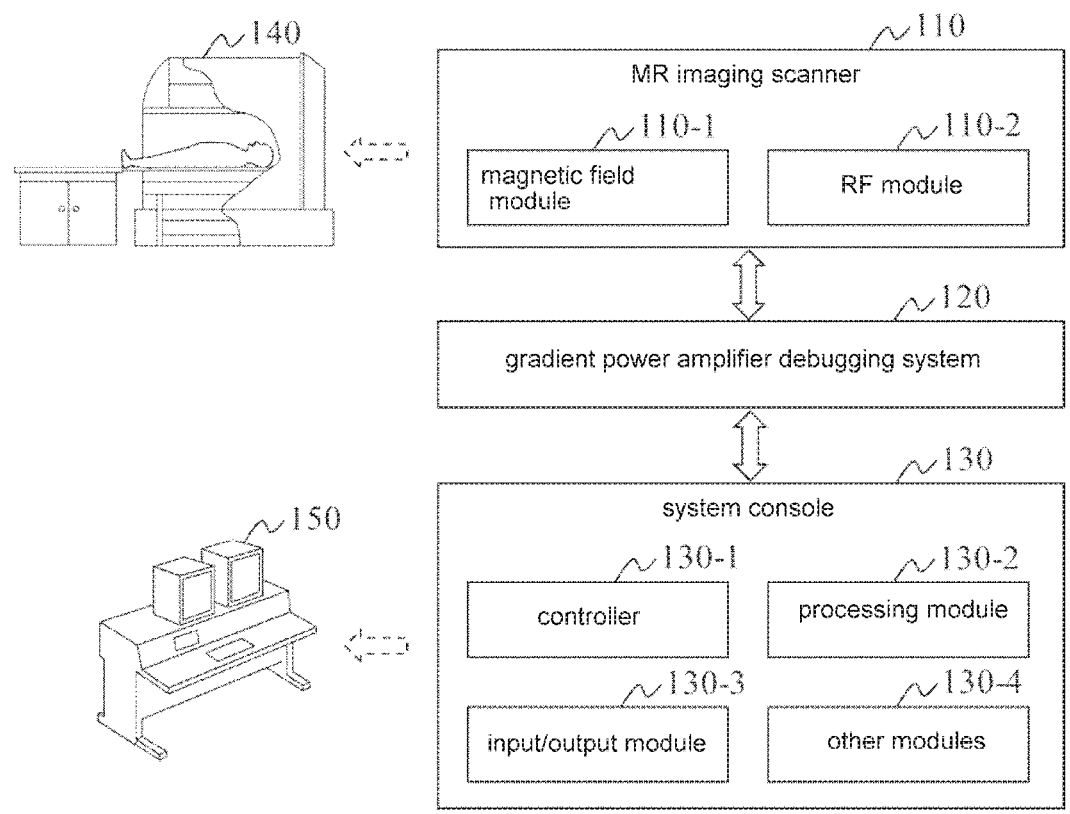
FIG. 1 is a schematic diagram of the MR debugging system shown in some examples of this application.

According to some embodiments of the present application, FIG. 1 shows a schematic diagram of an MR debugging system. An MR debugging system may comprise an MR imaging scanner 110, a gradient power amplifier debugging system 120, and a system console 130.

An MR imaging scanner 110 may scan a determined subject. The MR imaging scanner 100 may be used individually, or in combination with other devices (e.g. a PET-MRI device, or a SPECT-MRI device, etc.). In some embodiments, the MR imaging scanner 110 may comprise a magnetic field module 110-1, and an RF module 110-2.

The magnetic field module 110-1 may comprise a main magnetic field generator and/or a gradient magnetic field generator (not shown in FIG. 1). The main magnetic field generator may generate a static magnetic field $B_0$ during the process of MR imaging. In some embodiments, the main magnetic field generator may comprise various magnets, e.g., a permanent magnet, a superconducting electromagnet, or a resistive electro-magnet. In some embodiments, the main magnetic field generator may comprise a shimming coil. The gradient magnetic generator may generate gradient magnetic fields in X, Y and/or Z directions. The gradient magnetic field may spatially encoding the scanned subject. The gradient magnetic field generator may comprise a gradient coil. The gradient coil may be located in the main magnetic field or the shimming coil. The gradient coil may cause the main magnetic field to deform, thereby causing the direction of the magnetic field where the proton of the scanned subject are located varies with the position of the proton in the gradient field. The gradient coil may comprise an X coil, a Y coil, and/or a Z coil (not shown in FIG. 1). In some embodiments, the Z coil may be designed based on a circular (Maxwell) coil, while the X coil and the Y coil may be designed based on a saddle (Golay) coil. The X coil, Y coil and Z coil may generate magnetic fields in the X, Y and Z directions, so as to spatially encoding the scanned subject in the X, Y, and Z directions. The gradient coil may be coupled to the gradient power amplifier.

The RF module 110-2 may comprise an RF transmit coil and/or an RF receive coil (not shown in FIG. 1). The RF transmit coil may transmit an RF pulse signal to the scanned subject. The RF receive coil may receive an RF pulse signal from the scanned subject. In some embodiments, the magnetic field module 110-1, and/or the RF module 110-2 may vary in their functionality, size, types, shapes, locations, or quantity according to one or more specific conditions. For example, an RF coil may be classified as a volume coil and a local coil according to the difference in functionality and size. In some embodiments, a volume coil may comprise a birdcage coil, a transverse electromagnetic coil, a surface coil, or a saddle coil. In some embodiments, a local coil may comprise a birdcage coil, a solenoid coil, a saddle coil, or a flexible coil, etc. In some embodiments, the magnetic field module 110-1, and the RF module 110-2 may be designed as a tunnel type MR imaging scanner 140. The tunnel type MR imaging scanner 140 may comprise a close bore. The subject to be scanned may be positioned in the close bore, such that the tunnel MR imaging scanner 140 surrounds the subject to be scanned. In some embodiments, the magnetic field module 110-1, and the RF module 110-2 may be designed as an open type MR imaging scanner.

The gradient power amplifier debugging system 120 may comprise a gradient power amplifier. The gradient power amplifier may be coupled with the gradient coil in the magnetic field module 110-1. The gradient power amplifier may comprise an X gradient amplifier, a Y gradient amplifier, and/or a Z gradient amplifier. The gradient power amplifier may be coupled with a waveform generator. The waveform generator may generate a gradient waveform, which, after amplified by the X gradient amplifier, the Y gradient amplifier, and/or the Z gradient amplifier, delivers currents to the X coil, Y coil, and/or Z coil, respectively, so as to generate gradient magnetic fields in the X, Y and/or Z directions. The gradient power amplifier debugging system 120 may debug the gradient power amplifier. In some embodiments, the debugging may refer to testing, identifying, and/or adjusting, etc. parameters of the gradient power amplifier.

The system console 130 may control the MR debugging system. The system console 130 may comprise a controller 130-1, a processing module 130-2, an input/output module 130-3, and other modules 130-4. In some embodiments, the system console 130 may comprise an MR imaging table 150. The MR imaging table 150 and the MR imaging scanner 110 may be arranged in two separate rooms, with shielding walls in between for shielding and isolation purpose. In some embodiments, the system console 130 may comprise an external MR debugging system console (not shown in FIG. 1). The external MR debugging system console may be independent from the MR imaging table 150. The external MR debugging system console may comprise some interfaces. These interfaces may be interfaces to couple with the gradient coil in the magnetic field module 110-1, and/or the gradient power amplifier debugging system 120. In the process of MR debugging, the external MR debugging system console may couple with the MR debugging system via these interfaces for debugging control. After the debugging, the external MR debugging system console may be decoupled with these interfaces.

The controller 130-1 may control the magnetic field module 110-1 and the RF module 110-2 in the MR imaging scanner 110. The controller 130-1 may control the gradient power amplifier debugging system 120. The controller 130-1 may control the processing module 130-2, the input/output module 130-3, and/or the other modules 130-4. In some embodiments, the controller 130-1 may receive information from the MR imaging scanner 110, the gradient power amplifier debugging system 120, the processing module 130-2, the input/output module 130-3, and/or the other modules 130-4, and may transmit information to these systems, modules, or devices. In some embodiments, the controller 130-1 may comprise one or more computers, programs, algorithms, software, storage devices, interfaces, etc. The interfaces may comprise interfaces among the MR imaging scanner 110, the input/output module 130-3, the gradient power amplifier debugging system 120, the processing module 130-2, and/or the other modules 130-4.

In some embodiments, the controller 130-1 may receive commands from the user (e.g., the debugging operator, imaging technicians, etc.). The controller 130-1 may obtain commands from the user from the input/output module 130-3. The controller 130-1 may control the MR imaging scanner 110, the gradient power amplifier debugging system 120, the input/output module 130-3, and/or the processing module 130-2 by accepting the commands or translating the commands. For example, the controller 130-1 may process the input information from the user via the input/output module 130-3, and may translate the information into one or more corresponding commands. The commands may be a combination of one or more of debugging parameters, debugging timing, debugging methods of the gradient power amplifier debugging system 120. In some embodiments, the controller 130-1 may control the processing module 130-2 to choose one or more algorithms to process information of the gradient power amplifier debugging system 120.

The processing module 130-2 may process information from the MR imaging scanner 110, the gradient power amplifier debugging system 120, the controller 130-1, and/or the input/output module 130-3. The processing module 130-2 may process the information, by employing one or more algorithms, e.g., data transformation, signal filtering, and/or numerical computation, etc. In some embodiments, the processing module 130-2 may generate control signal related to the gradient power amplifier debugging system 120. In some embodiments, data results with and/or without the processing by the processing module 130-2 may be sent to respective modules or units in the MR debugging system. In some embodiments, the processing module 130-2 may provide storage function for the unprocessed and/or processed information. In some embodiments, the information processed by the processing module 130-2 may be sent to respective memories (not shown in FIG. 1) for storage, and then retrieved by respective modules or units in the MR debugging system, or further processed by the processing module 130-2.

The input/output module 130-3 may receive, send, or display information. In some embodiments, the input/output module 130-3 may comprise one or more of a keyboard, a haptic device, a mouse, an audio input device, an image input device, and a remote control device, etc. The information input/output by the input/output module 130-3 may comprise a combination of one or more of a program, a software, an algorithm, data, signal, text, a number, an image, audio, etc. In some embodiments, the user may input some debugging parameters, or set initialization conditions for the gradient power amplifier debugging system 120. In some embodiments, some input information may come from external data sources (e.g., a combination of one or more of a floppy disk, a hard disk, an optical disc, a memory chip, a wireline terminal, a wireless terminal, etc.). The input/output module 130-3 may receive information from respective modules or units in the MR debugging system, and may send information to respective modules or units in the MR debugging system. In some embodiments, the input/output module 130-3 may transmit the information to the other modules 130-4 for corresponding operation, e.g., storage, printing, display, or alert, etc. In some embodiments, the input/output module 130-3 may comprise a graphic user interface, for presenting relevant information (e.g., a combination of one or more of system parameters, debugging parameters, current/voltage waveform curves, process of debugging, progress of debugging, results of debugging, performance of debugging, etc.) in the process of debugging. The graphic user interface may prompt the user to input parameters, and may involve the user into the information processing process (e.g., starting or stopping the debugging process, selecting or modifying debugging parameters, selecting or modifying algorithms, modifying the program, exiting the system, system upgrade, or system update, etc.).

Other modules 130-4 may comprise one or more terminals with functionality such as storing, displaying, alarming, or printing, such as a combination of one or more of a display screen, a printer, a storage device, a reading device, a signaling light, a speaker, a computing device, etc. In some embodiments, the other modules 130-4 may comprise a database (not shown in FIG. 1). In some embodiments, the other modules 130-4 may comprise a network (not shown in FIG. 1). The network may be a single network, or may be a combination of multiple various networks. For instance, it may be a local area network (LAN), a wide area network (WAN), a public network, a private network, a public switched telephone network (PSTN), internet, a wireless network, a virtual network, or any combination thereof. In some embodiments, the other modules 130-4 may comprise one or more terminals connected to the network(not shown in FIG. 1). The user may implement control on the MR debugging system via the terminals.

In some embodiments, the MR imaging scanner 110, the gradient power amplifier debugging system 120, and/or the system console 130 may couple to each other either directly or indirectly. In some embodiments, the MR imaging scanner 110, the gradient power amplifier debugging system 120, and/or the system console 130 may couple to each other via a network directly. In some embodiments, the MR imaging scanner 110, the gradient power amplifier debugging system 120, and/or the system console 130 may couple to each other indirectly via one or more intermediate modules (not shown in FIG. 1). Such intermediate modules may be entity or non-entity (e.g. one or more of radio wave, optical, acoustic, electromagnetic, etc.). Various modules and units may be coupled via wireless and/or wireline ways.

It should be noted that the above description of the MR debugging system is only convenient and does not limit this application to the scope of the embodiments cited. It is understandable that for those skilled in the art, after understanding the principles of the system, it may be possible, without departing from this principle, to make arbitrary combinations of modules, or to connect subsystems with other modules, to make various formal and detailed repairs to the application areas in which the above-mentioned methods and systems are implemented. Positive and change.

Figure 2:
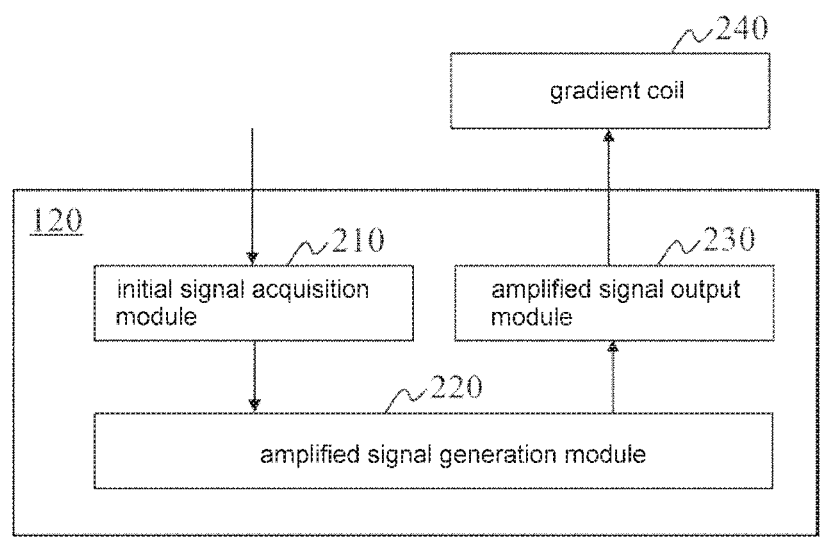
FIG. 2 is a schematic diagram of a gradient power amplifier debugging system in accordance with some embodiments of the present application.

According to some embodiments of the present application, FIG. 2 shows a schematic diagram of the gradient power amplifier debugging system 120. The gradient power amplifier debugging system 120 may comprise an initial signal acquisition module 210, an amplified signal generation module 220, and an amplified signal output module 230.

The initial signal acquisition module 210 may acquire an initial signal. In some embodiments, the initial signal may be a current signal, or a voltage signal. In some embodiments, the initial signal may be a DC signal, or an AC signal. In some embodiments, the initial signal may be a digital signal, or an analog signal. In some embodiments, the initial signal may be a pulse signal. In some embodiments, the initial signal may comprise one or more waveforms. The waveforms may be a rectangle wave, a triangle wave, a trapezoidal wave or any combination thereof. In some embodiments, the initial signal may act as an input signal to the gradient power amplifier debugging system 120. In some embodiments, the initial signal may be used by the amplified signal generation module 220 to generate an amplified signal, which is output to the gradient coil 240 to generate a gradient magnetic field, such that the initial signal may also be referred to as a gradient waveform. In some embodiments, the gradient waveform may have a shape of a trapezoidal wave. A waveform may involve some characteristic parameters. For example, a trapezoidal wave may comprise one or more of a rising time, an amplitude, and an amplitude duration, etc.

The amplified signal generation module 220 may generate an amplified signal. The amplified signal generation module 220 may comprise a gradient power amplifier. In some embodiments, the amplified signal generation module 220 may comprise one or more analog signal operational amplifiers, one or more digital signal processing sub-modules, etc. The analog signal operational amplifier may comprise a combination of one or more of a proportional operation circuit, a summing circuit, an integral and differential circuit, a logarithmic and exponential circuit, a multiplication and division circuit, etc. The digital signal processing sub-module may process the digital signals, e.g., amplification, filtering, etc.

In some embodiments, the amplified signal may be a current signal, or a voltage signal. In some embodiments, the amplified signal may be a DC signal, or an AC signal. In some embodiments, the amplified signal may be a digital signal, or an analog signal. In some embodiments, the amplified signal may be a pulse signal. In some embodiments, the amplified signal may comprise one or more waveforms. The waveforms may be a rectangle wave, a triangle wave, a trapezoidal wave or any combination thereof. The generation of the amplified signal may be based on the initial signal. In some embodiments, the amplified signal generation module 220 may amplify the initial signal to produce the amplified signal. In some embodiments, the amplified signal and the initial signal may be similar signals. For example, both the amplified signal and the initial signal may be current signals, or voltage signals. As another example, both the amplified signal and the initial signal may be digital signals, or analog signals. In some embodiments, the amplified signal and the initial signal may be different signals. For example, the initial signal may be a digital signal, while the amplified signal may be an analog signal. As another example, the initial signal may be a digital signal, while both the amplified signal may be a current signal. In some embodiments, the amplified signal and the initial signal may be of similar waveforms. For example, both the initial signal and the amplified signal may be trapezoidal signals. In some embodiments, the amplified signal and the initial signal may be of different waveforms. For example, the initial signal may be a rectangle wave, while the amplified signal may be a trapezoidal signal. In some embodiments, the amplified signal and the initial signal may comprise different waveform characteristic parameters. For example, both the amplified signal and the initial signal may be trapezoidal waveforms, but are different in terms of their rising times, amplitude, and amplitude durations, etc. In some embodiments, the amplitude of the amplified signal may be greater than that of the initial signal.

The amplified signal output module 230 may output the amplified signal to the gradient coil 240. In some embodiments, the trapezoidal coil 240 may be located in the magnetic field module 110-1. The amplified signal output module 230 may comprise an interface between the gradient power amplifier debugging system 120 and the gradient coil 240. In some embodiments, the amplified signal output module 230 may comprise one or more wires for outputting the amplified signal to the gradient coil 240.

It should be noted that the above description of the gradient power amplifier debugging system 120 is only a concrete example and should not be considered the only feasible implementation. Each of the above modules can be implemented by one or more components, and the functions of each module are not limited to this. The above modules can be added or deleted according to specific implementation scenarios or needs. Obviously, for professionals in the art, it is possible, without departing from the basic principles of the gradient power amplifier, to make various modifications and changes in form and detail to the specific implementation of the gradient power amplifier debugging system 120, and to make some simple deductions or substitutions. The order of each module is adjusted or combined without creative effort, but these modifications and changes are still within the scope described above. For example, in some embodiments, the amplified signal output module 230 may comprise one or more processing sub-modules for further processing the amplified signal and outputting the processed signal to the gradient coil 240. As another example, in some embodiments, the amplified signal output module 230 may be combined with the amplified signal generation module 220 into an independent module. As another example, in some embodiments, the amplified signal output module 230 may be omitted and the amplified signal generation module 220 may be coupled directly to the gradient coil 240. As a further example, in some embodiments, a storage module may be introduced for storing the initial signal or the amplified signal, etc. As a further example, in some embodiments, the gradient power amplifier debugging system 120 may further comprise a power supply module, or a cooling module, etc.

Figure 3:
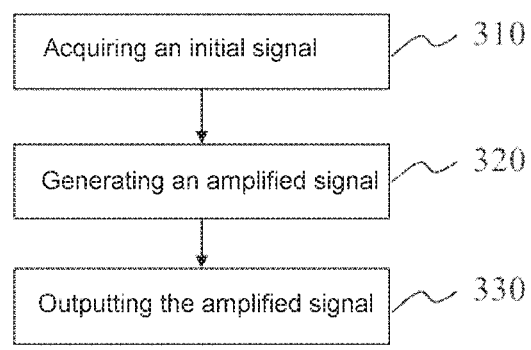
FIG. 3 is an exemplary flow chart for the debugging of a gradient power amplifier shown in some embodiments of the present application.

According to some embodiments of the present application, FIG. 3 shows an exemplary flow diagram for gradient power amplifier debugging. The process of gradient power amplifier debugging may comprise acquiring an initial signal 310, generating an amplified signal 320, and outputting the amplified signal 330.

In step 310, an initial signal may be acquired. In some embodiments, the initial signal may be obtained from a waveform generator. The waveform generator may be located in the MR imaging scanner 110, the gradient power amplifier debugging system 120, or the system console 130. In some embodiments, the initial signal may be stored in one or more memories in advance, from which the initial signal may be read directly in step 310. In some embodiments, the memories may be located in the MR imaging scanner 110, the gradient power amplifier debugging system 120, or the system console 130. Step 310 may be performed by the initial signal acquisition module 210.

In step 320, an amplified signal may be generated. The generation of the amplified signal may be based on the initial signal as acquired in step 310. The amplified signal may be a signal generated by linearly amplifying, or non-linearly amplifying the initial signal. In some embodiments, the initial signal may be amplified more than once. The amplified signal may be generated by one or more analog signal operational amplifiers, one or more digital signal processing sub-modules, etc. In some embodiments, the analog signal may be transformed into a digital signal for amplification. In some embodiments, the digital signal may be transformed into a analog signal for amplification. In some embodiments, the current signal may be transformed into a voltage signal for amplification. In some embodiments, the voltage signal may be transformed into a current signal for amplification. Step 320 may be performed by the amplified signal generation module 220.

In step 330, the amplified signal as generated in step 320 may be output. The amplified signal may be output to the gradient coil 240. In some embodiments, the amplified signal may be transmitted via one or more wires to the gradient coil 240. Step 330 may be performed by the amplified signal output module 230.

It should be noted that the above description of the debugging process of the gradient power amplifier is only a concrete example and should not be considered as the only feasible implementation. The above steps can be selected to add or delete according to specific implementation scenarios or needs. Obviously, for professionals in the field, after understanding the basic principles of the gradient power amplifier, it is possible to make various modifications and changes in the form and details of the specific implementation methods and steps of the gradient power amplifier debugging without departing from this principle, and to make some simple deductions or substitutions. The sequence of steps is adjusted or combined without creative effort, but these modifications and changes are still within the scope described above. For example, step 330 can be omitted. For example, step 330 can be executed in step 320.

According to some embodiments of the present application, FIG. 4-A shows a schematic diagram of the amplified signal generation module 220. The amplified signal generation module 220 may comprise a control sub-module 401, a signal modulation sub-module 402, an amplification circuit sub-module 403, and a signal processing sub-module 404. In addition to the above mentioned sub-modules, the amplified signal generation module 220 may further comprise one or more other sub-modules. FIG. 4-A exemplifies the connections between the various sub-modules, but the connections between the various sub-modules are not limited thereto.

The control sub-module 401 may control the various sub-modules in the amplified signal generation module 220. In some embodiments, the control sub-module 401 may control input signals and/or output signals to or from the various sub-modules of the amplified signal generation module 220. In some embodiments, the control sub-module 401 may identify, and/or adjust the signals in the signal modulation sub-module 402, the amplification circuit sub-module 403, and the signal processing sub-module 404. In some embodiments, the control sub-module 401 may control the signals such that the amplified signal generated by the amplified signal generation module 220 can meet the requirements of the gradient power amplifier on the signal linearity, accuracy, response time, or bandwidth. In some embodiments, the control sub-module 401 may comprise one or more internal controllers, e.g. a feedforward controller, and/or a feedback controller. The internal controller may comprise one or more proportional, integral and/or differential controller, e.g., a PI controller, a PID controller, etc. In some embodiments, the control sub-module 401 may comprise one or more filters, e.g., an analog filter, a digital filter, a high-pass filter, a low-pass filter, a band-pass filter, a band-stop filter, a passive filter, or an active filter, etc.

In some embodiments, the control sub-module 401 may implement parameter self-tuning function of the gradient power amplifier. The parameters may comprise parameters of the load (e.g., the gradient coil 240) of the gradient power amplifier, e.g., load impedance, and load inductance, etc. The parameters may comprise control parameters of the control sub-module 401. The control parameters may comprise parameters in a transfer function related to the internal controller, e.g. a proportional coefficient, an integration coefficient, or a differentiation coefficient, etc. The control parameters may also comprise parameters related to a filter, e.g., central frequency, stop frequency, bandwidth of the pass band, ripple, inband standing wave ratio, stopband rejection, delay, inband phase linearity, etc., of the filter Tuning may refer to identification and/or adjustment to one or more parameters. Identification may refer to tracking, testing, or acquiring of a certain parameter so as to know the value thereof. In some embodiments, the value of the load impedance, and/or the load inductance may be identified. In some embodiments, the identified parameter may be the real value or an estimated value of the parameter. The adjustment may refer to adjusting, or modifying the value of a certain parameter, so as to change the current value of the parameter to another value. In some embodiments, the values of one or more control parameters may be adjusted. In some embodiments, the adjusted values may be those obtained via one or more computations, or may be one or more fixed constant values.

In some embodiments, the control sub-module 401 may implement load adaptation function of the gradient power amplifier. Load adaptation may refer to the capability of an amplified signal generated by the amplified signal generation module 220, still meeting the requirements that the gradient power amplifier has on signal linearity, accuracy, response time, or bandwidth, etc, when the gradient power amplifier is coupled to different loads. In some embodiments, the control sub-module 401 may implement load adaptation function in a relative wide range. For example, the control sub-module 401 may adapt to a load of inductance of 400 μH, a load of inductance of 1 mH, and a load of inductance in the range of 400 μH-1 mH.

The signal modulation sub-module 402 may modulate the signal. Signal modulation may refer to employ a modulating signal for comparison to a carrier signal, such that the chopped signal resulted from the comparison has one or more of its parameters (e.g., amplitude, frequency, or phase, etc.) vary according to the values of the parameters of the modulating signal after being filtered. In some embodiments, the output signal from the control sub-module 401 may be used as the modulating signal, while the modulated carrier signal may be used as a driving signal for the amplification circuit sub-module 403.

The amplification circuit sub-module 403 may amplify the signal. The amplification circuit sub-module 403 may comprise an amplification circuit. The amplification circuit may amplify an analog signal, or a digital signal. The amplification circuit may amplify a current signal, or a voltage signal. In some embodiments, the amplification circuit may comprise a concatenation circuit multistage amplifying the signal.

The signal processing sub-module 404 may process the signal. Signal processing may comprise filtering the signal to improve signal quality, e.g., to improve SNR, to reject resonance, etc. In some embodiments, the signal processing sub-module 404 may comprise one or more filters (e.g., an analog filter, a digital filter, a high-pass filter, a low-pass filter, a band-pass filter, a band-stop filter, a passive filter, or an active filter, etc.).

According to some embodiments of the present application, FIG. 4-B shows an exemplary flow diagram of amplified signal generation. The process of amplified signal generation may comprise controlling a signal 411, modulating the signal 412, amplifying the signal 413, and processing the signal 414.

In step 411, a signal may be controlled. In some embodiments, the signal to be controlled may be the initial signal as acquired in step 310, the intermediate signal as generated in step 320, etc. In some embodiments, the signal to be controlled may be a signal retrieved from the control sub-module 401, the signal modulation sub-module 402, the amplification circuit sub-module 403, and/or the signal processing sub-module 404. In some embodiments, step 411 may identify, and/or adjust parameters, etc., in the control sub-module 401, the signal modulation sub-module 402, the amplification circuit sub-module 403, and/or the signal processing sub-module 404. In some embodiments, step 411 may control the input signals, and/or output signals to or from the control sub-module 401, the signal modulation sub-module 402, the amplification circuit sub-module 403, and/or the signal processing sub-module 404. In some embodiments, step 411 may tune load impedance, load inductance, control parameters, etc. In some embodiments, step 411 may adapt to different loads by adjusting the control parameters. Step 411 may be carried out by the control sub-module 401.

In step 412, a signal may be modulated. In some embodiments, the signal to be modulated may be a signal as controlled by step 411. In some embodiments, the signal to be modulated may be a signal retreived from the control sub-module 401, the signal modulation sub-module 402, the amplification circuit sub-module 403, and/or the signal processing sub-module 404, after being controlled in step 411. Step 412 may be carried out by the signal modulation sub-module 402.

In step 413, a signal may be amplified. Signal amplification may be based on the result of signal modulation in step 412. In some embodiments, the signal modulated in step 412 may be amplified directly. In some embodiments, a signal may be retrieved from the control sub-module 401, the signal modulation sub-module 402, the amplification circuit sub-module 403, and/or the signal processing sub-modulation 404, according to one or more parameters (e.g., amplitude, frequency, phase, pulse width, etc.) after signal modulation, and then amplified. Step 413 may be carried out by the amplification circuit sub-module 403.

In step 414, a signal may be processed. Signal processing may be based on the amplified signal in step 413. In some embodiments, the amplified signal may be filtered more than once. Step 414 may be carried out by the signal processing sub-module 404. In some embodiments, it may be determined whether the signal processed in step 414 meets the requirements that the gradient power amplifier has on signal linearity, accuracy, response time, or bandwidth. If these requirements are met, the signal may be output to the gradient coil 240 in step 330. If these requirements are, however, not met, the amplified signal generation process may go back to step 411 for further operations of signal controlling, modulation, amplification, processing, etc. In some embodiments, the process of determination may be performed in step 414. In some embodiments, the process of determination may be performed in step 411.

It should be noted that the above description of the amplified signal generation module 220 and the amplified signal generation process is only a concrete example and should not be considered as the only feasible implementation. Each of the above sub-modules can be implemented by one or more components, and the functions of each sub-module are not limited to this. The above sub modules can be added or deleted according to specific implementation scenarios or needs. Obviously, for professionals in the field, after liberating the basic principles of large signal generation, various modifications and changes in the form and details of the specific implementation methods and steps of amplified signal generation may be made without departing from this principle, and some simple deductions or substitutions may be made without payment. Under the premise of creative labor, the order of each sub-module and/or each processing step is adjusted or combined, but these modifications and changes are still within the scope described above. For example, the signal processing sub module 404 can be combined into a module with the control sub module 401. For example, you can add a signal judgment step to judge the signal processed in step 414.

According to some embodiments of the present application, FIG. 5-A shows a schematic diagram of the control sub-module 401. The control sub-module 401 may comprise a control unit 501, an initialization unit 502, a data retrieval unit 503, a load parameter identification unit 504, a control parameter adjustment unit 505, and a storage unit 506. In addition to the above mentioned units, the control sub-module 401 may further comprise one or more other units.

FIG. 5-A exemplifies the connections between the various modules, but the connections between the various modules are not limited thereto.

The control unit 501 may control the signal. In some embodiments, the control unit 501 may control the input signals, and/or output signals to or from the signal modulation sub-module 402, the amplification circuit sub-module 403, and/or the signal processing sub-module 404. The control unit 501 may comprise a feedforward control sub-unit 501-1, and a close-loop control sub-unit 501-2.

The feedforward control sub-unit 501-1 may introduce information related to the load parameters (e.g., the load impedance, or the load inductance, etc.) into the control unit 501. In some embodiments, the feedforward control sub-unit 501-1 may predict the load parameters in advance. For example, the feedforward control sub-unit 501-1 may have a load model set therein which is related to the load parameters. The feedforward control sub-unit 501-1 may control the signal directly via the load model. In some embodiments, the feedforward control sub-unit 501-1 may estimate the possible output signal of the gradient power amplifier based on the load model and the input signal to the gradient power amplifier.

The close-loop control sub-unit 501-2 may feed back the output signal from the gradient power amplifier to the control unit 501. The close-loop control sub-unit 501-2 may control the signal according to the difference between the required output signal and the actual output signal. In some embodiments, the close-loop control sub-unit 501-2 may comprise a proportional controller, an integral controller, or a differential controller, or any combination thereof, e.g., a PI controller, a PD controller, or a PID controller. In some embodiments, the proportional integral (differential) control sub-unit 501-3 may comprise one or more PI controllers or PID controllers. In some embodiments, the close-loop control sub-unit 501-2 may comprise one or more filter sub-units 501-4. The filter sub-unit 501-4 may filter the signal in the close-loop control sub-unit 501-2 and to improve SNR, to reject resonance, etc.

The initialization unit 502 may perform initialization operation for the control sub-module 401. The initialization may comprise initializing the parameters of the various units in the control sub-module 401. The parameters to be initialized may comprise relevant parameters in the control unit 501, the data retrieval unit 503, the load parameter identification unit 504, the control parameter adjustment unit 505, or the storage unit 506.

The data retrieval unit 503 may retrieve the data in the control unit 501. The retrieved data may comprise data related to the feedforward control sub-unit 501-1, the close-loop control sub-unit 501-2, the proportional integral (differential) control sub-unit 501-3, or the filter sub-unit 501-4. The retrieved data may be data in these sub-units, or the input thereto, and/or the data in the output signals. In some embodiments, the retrieved data may be data that is scaled up, integral data, or differential data, etc., or any combination thereof. In some embodiments, the data retrieval unit 503 may retrieve the data in the storage unit 506. In some embodiments, the data retrieval unit 503 may store the retrieved data in the storage unit 506.

The load parameter identification unit 504 may identify the load parameters. In some embodiments, the load parameters may comprise the load impedance, or the load inductance, etc. The control parameter adjustment unit 505 may adjust the control parameters. In some embodiments, the control parameters to be adjusted may comprise the parameters in the proportional integral (differential) control sub-unit 501-3, or the filter sub-unit 501-4. For example, the parameters may be the proportional coefficiencies, the integral coefficiencies, the differential coefficiencies, or the parameters of the filters. In some embodiments, the data retrieval unit 503, the load parameter identification unit 504, and the control parameter adjustment unit 505 may implement the parameter self-tuning functionality, and/or the load adaptation functionality of the control sub-module 401 in conjunction.

The storage unit 506 may store data or information related to the control unit 501, the initialization unit 502, the data retrieval unit 503, the load parameter identification unit 504, and/or the control parameter adjustment unit 505. The stored data may comprise data generated by the above mentioned units. In some embodiments, these units may obtain data from the storage unit 506. The stored data may be text, numerical values, image information, etc. The storage unit 506 may comprise one or more memories.

According to some embodiments of the present application, FIG. 5-B shows an exemplary flow diagram of signal control. In some embodiments, the signal control process may achieve the parameter self-tuning functionality, and/or load adaptation functionality, etc. of the control sub-module 401. In some embodiments, the signal control process may comprise initializing 512, retrieving data 513, identifying load parameters 514, and adjusting control parameters 515.

In step 512, initialization operation may be performed. Initialization may comprise initializing the control unit 501, the data retrieval unit 503, the load parameter identification unit 504, the control parameter adjustment unit 505, or the storage unit 506. The initialization may comprise assigning initial values to the parameters or data in the above-mentioned units. In some embodiments, the initialization may comprise setting an initial status for the control approach, or computing method, etc. that may be of use in the above mentioned units. For example, the load model utilized in the feedforward control sub-unit 501-1 may be chosen. As another example, the filter utilized in the filter sub-unit 501-4 may be chosen. As a further example, the computing methods in the load parameter identification unit 504, and/or the control parameter adjustment unit 505 may be chosen. The initialization may be fully automated, semi-automated, or manual. For instance, the initialization may be performed automatically according to one or more programs. As another example, the user may manually input one or more parameters via the graphic user interface in the input/output module 130-3. In some embodiments, the control unit 501 may perform initialization setup on the feedforward control sub-unit 501-1, or the close-loop control sub-unit 501-2 via the control parameter adjustment unit 505. Step 512 may be carried out by the initialization unit 502.

In step 513, data may be retrieved. Data retrieval may be based on the control information in the control unit 501. In some embodiments, the control information may comprise information relevant to the load model utilized in the feedforward control sub-unit 501-1. In some embodiments, the control information may comprise information in the proportional integral (differential) control sub-unit 501-3, e.g. the data that is scaled up, integral data, or differential data, etc., or any combination thereof. In some embodiments, the retrieved data may come from the characteristic output from the proportional integral (differential) control sub-unit 501-3. The characteristic output may be representative of the difference between the output signal and the input signal of the gradient power amplifier debugging system 120. The characteristic output may comprise an integral output, a proportional output, and/or a differential output of the PI or PID (simply, PI(D)) controller. In some embodiments, the control information may comprise information in the filter sub-unit 501-4, e.g., the parameters of the filters, or the signal after filtering, etc. Step 513 may be carried out by the data retrieval unit 503.

In step 514, load parameters may be identified. The identification of the load parameters may be based on the data retrieved in step 513. In some embodiments, the retrieved data may undergo one or more computations, resulting in values related to the load parameters. The values related to the load parameters may be values of the load parameters, or the change in the values of the load parameters. In some embodiments, the identification of the load parameters may be based on data retrieved in two or more times, for example, may be based on the integral values, or differential values that are retrieved in two times. Step 514 may be carried out by the load parameter identification unit 504.

In step 515, control parameters may be adjusted. The adjustment to the control parameters may be based on the load parameters identified in step 514. In some embodiments, the load parameters identified in step 514 may undergo one or more computations, and then the values of the control parameters may be adjusted according to the result of computation. In some embodiments, after adjusting the control parameters, the signal control process may go back to step 513 for further operations of data retrieval, load parameter identification, control parameter adjustment, etc. Step 515 may be carried out by the parameter adjustment unit 505.

It should be noted that the above description of control sub-module 401 and signal control flow is only a concrete example and should not be considered as the only feasible implementation. Each of the above-mentioned units or sub-units can be implemented by one or more components, and the functions of each unit or subunit are not limited to this. The units or sub units mentioned above can be added or deleted according to specific implementation scenarios or needs. Obviously, for professionals in the field, after understanding the basic principles of signal control, various modifications and changes in form and detail may be made to the specific embodiments and steps of signal control without departing from this principle, and some simple deductions or substitutions may be made without creative effort. On the premise of labor, some adjustments or combinations are made to each unit or subunit, and the order of the processing steps, but these modifications and changes are still within the scope described above. For example, the storage unit 506 can be combined in other module 130-4. For example, initialization unit 502, and/or initialization step 512 can be omitted. Again, one or more data storage steps can be added between steps 512, 513, 514, and 515. For example, after step 515, a judgment step can be added to determine whether the signal meets the requirements of a gradient power amplifier.

According to some embodiments of the present application, FIG. 6-A shows a schematic diagram of the load parameter identification unit 504. The load parameter identification unit 504 may identify the load parameters. The load parameter identification unit 504 may identify parameters such as a load impedance, and a load inductance, etc. In some embodiments, the load parameter identification unit 504 may comprise a load impedance identification sub-unit 601, and a load inductance identification unit 602.

The load impedance identification unit 601 may identify the load impedance. In some embodiments, the load impedance may refer to the line impedance, e.g., the coil resistance r in FIG. 16. In some embodiments, the load impedance may refer to the impedance relevant to the load model in the feedforward control sub-unit 501-1. In some embodiments, the load impedance identification sub-unit 601 identifies impedance which may be a real value, an estimated value of the load impedance, or change in the value of the load impedance.

The load inductance identification sub-unit 602 may identify the load inductance. In some embodiments, the load inductance may refer to the inductance of the gradient coil 240, e.g., the coil resistance $L_{coil}$ in FIG. 16. In some embodiments, the load inductance may refer to the inductance relevant to the load model in the feedforward control sub-unit 501-1. In some embodiments, the load inductance identification sub-unit 602 identifies inductance which may be a real value, an estimated value of the load inductance, or change in the value of the load inductance.

According to some embodiments of the present application, FIG. 6-B shows an exemplary flow diagram of load parameter identification. The load parameter identification process may comprise identifying the load impedance 611, and identifying the load inductance 612.

In step 611, load impedance may be identified. In some embodiments, step 611 may be based on the information initialized in step 512, and/or information retrieved in step 513. In some embodiments, step 611 may comprise retrieving data from the storage unit 506, and then identifying load impedance based on this data. The identification of the load impedance may be based on one or more formulae. In some embodiments, the identification of the load impedance may be based on data retrieved in two or more times.

In step 612, load inductance may be identified. In some embodiments, step 612 may be based on the information initialized in step 512, and/or information retrieved in step 513. In some embodiments, step 612 may also comprise retrieving data from the storage unit 506, and then identifying load inductance based on this data. The identification of the load inductance may be based on one or more formulae. In some embodiments, the identification of the load inductance may be based on data retrieved in two or more times. In some embodiments, the identification of the load inductance may be based on the load impedance identified in step 611. In some embodiments, after identifying the load impedance in step 611, control parameters may be adjusted in step 515, and then data may be retrieved by going back to step 513. The identification of the load inductance may be based on computation on the data retrieved after the control parameters are adjusted.

As noted, the above description of the load parameter identification unit 504 and the process of load parameter identification are merely specific examples, rather than the only viable embodiment. Each of the above mentioned sub-units may be implemented by one or more parts, and the functionality of each of the sub-units is not limited thereto. The above mentioned various sub-units may be added or deleted according to the specific implementing scenario or requirements. Apparently, when appreciating the basic principles of load parameter identification, those skilled may make various modification and changes to the specific embodiments and steps of the load parameter identification in terms of forms and details without departing from these principles, make some simple inference and substitution without creative work, and make some adjustment or combination to the ordering of the various sub-units, and/or processing steps, where these modification and changes are still within the scope of the present disclosure. For example, in some embodiments, the load impedance sub-unit 501 and/or step 611 may be omitted. As another example, in some embodiments, a control parameter adjustment step, and/or data retrieval step may be added between step 611 and step 612.

According to some embodiments of the present application, FIG. 7-A shows a schematic diagram of the control parameter adjustment unit 505. The control parameter adjustment unit 505 may adjust the control parameters. The control parameter adjustment unit 505 may adjust parameters which may comprise the control parameters in the proportional integral (differential) control sub-unit 501-3, e.g., the proportional coefficient, the integral coefficient, the differential coefficient, etc. The parameters that are adjusted by the control parameter adjustment unit 505 may comprise the parameters of the filters in the filter sub-unit 501-4. In some embodiments, the control parameter adjustment unit 505 may comprise a PI(D) control parameter adjustment sub-unit 701, a load adaptation sub-unit 702, and a checking sub-unit 703.

The PI(D) control parameter adjustment sub-unit 701 may adjust the PI(D) control parameters. In some embodiments, the PI(D) control parameter may comprise a proportional coefficient, an integral coefficient, or a differential coefficient, etc., of the PI(D) controller in the proportional integral (differential) control sub-unit 501-3. The load adaptive sub-unit 702 may automatically adapt the gradient power amplifier to loads of different inductance. In some embodiments, the load adaptive sub-unit 702 may achieve the load adaptation functionality by adjusting the parameters of one or more filters in the filter sub-units 501-4. In some embodiments, the filters may comprise one or more set of parameter design scheme, which may exist in one or more filters. For example, a filter and a parameter design scheme may have a one-to-one correspondence. As another example, a filter may have two or more parameter design schemes. In some embodiments, a filter may be a low-pass filter, which allows the signal components in the low band to pass; and the filter may switch among cutoff frequency parameters automatically according to the result of calculation and/or testing in the load parameter identification step 514, and/or the control parameter adjustment step 515, so as to adapt to the load in a broader range of inductance. The checking sub-unit 703 may test and/or evaluate the result of control parameter adjustment.

According to some embodiments of the present application, FIG. 7-B shows an exemplary flow diagram of control parameter adjustment. The control parameter adjustment process may comprise adjusting the PI(D) control parameter 711, adjusting the filter parameters 712, and checking 713.

In step 711, PI(D) control parameters may be adjusted. The PI(D) control parameters may comprise proportional coefficients, integral coefficients, and/or differential coefficients. In some embodiments, adjustment to the PI(D) control parameters may be based on the load impedance identified in step 611, and/or the load inductance identified in step 612. In some embodiments, the load impedance, and/or the load inductance may be calculated, so as to obtain the values of the proportional coefficient, the integral coefficient, and/or the differential coefficient, and then the proportional coefficients, the integral coefficients, and/or the differential coefficients in the PI(D) controller are adjusted to the calculated values. Step 711 may be carried out by the PI(D) control parameter adjustment sub-unit 701.

In step 712, the parameters of the filters may be adjusted. The parameters of a filter may comprise a central frequency, a stop frequency, a bandwidth of the pass band, a ripple, an inband standing wave ratio, stopband rejection, a delay, an inband phase linearity, etc., of the filter. In some embodiments, the adjustment to the filter parameters may be based on the load impedance identified in step 611, and/or the load inductance identified in step 612. In some embodiments, the values of the filter parameters may be obtained by calculation on the basis of the load impedance and/or the load inductance, and the corresponding parameters of the filters may then be adjusted thereto. In some embodiments, a filter may be selected from two or more filters according to the values of the identified load impedance and/or load inductance based on one or more selecting criteria, as the filter employed in the filter sub-unit 501-4. The selecting criteria may be one or more thresholds, or one or more judging conditions, etc. Step 712 may be carried out by the load adaptation sub-unit 702.

In step 713, the result of control parameter adjustment may be checked. In some embodiments, the checking may comprise, after the performance of step 711 and/or 712, re-retrieving the data, the data retrieved may comprise data after scaling up, integral data, differential data, or filtered data, etc., or any combination of the above. In some embodiments, one or more characteristic data may be retrieved from the above mentioned data, e.g., a maximum and/or a minimum, etc. of the integral data or differential data, etc. In some embodiments, the result of control parameter adjustment may be evaluated according to the retrieved characteristic data, and one or more evaluation criteria. The evaluation criteria may be one or more thresholds, or one or more judging conditions, etc. In some embodiments, the retrieved characteristic data may be further calculated and then evaluated. Step 713 may be carried out by the checking sub-unit 703.

As noted, the above description of the control parameter adjustment unit 505 and the process of control parameter adjustment are merely specific examples, rather than the only viable embodiment. Each of the above mentioned sub-units may be implemented by one or more parts, and the functionality of each of the sub-units is not limited thereto. The above mentioned various sub-units may be added or deleted according to the specific implementing scenario or requirements. Apparently, when appreciating the basic principles of control parameter adjustment, those skilled may make various modification and changes to the specific embodiments and steps of the control parameter adjustment in terms of forms and details without departing from these principles, make some simple inference and substitution without creative work, and make some adjustment or combination to the ordering of the various sub-units, and/or processing steps, where these modification and changes are still within the scope of the present disclosure. For instance, the load adaptation sub-unit 702, the checking sub-unit 703, step 712, and/or step 713 may be omitted. As another example, after step 713, the control parameter adjustment process may return to step 711, and performs further control parameter adjustment operation according to the checking result of step 713.

According to some embodiments of the present application, FIG. 8 shows a schematic diagram of an embodiment of the control sub-module 401. In some embodiments, the control sub-module 401 may comprise a feedforward controller 802, a proportional controller 803, an integration controller 804, and a low-pass filter 806. The control sub-module 401 may comprise an input waveform signal 801. In some embodiments, the control sub-module 401 may be coupled to a hardware amplification circuit 805. The output signal from the hardware amplification circuit 805 may be the output signal of the gradient power amplifier, which may be output to the gradient coil 240. In some embodiments, the hardware amplification circuit 805 may comprise one or more amplification circuits and/or filters, etc. In some embodiments, the hardware amplification circuit 805 may refer to a simulation or emulation of the hardware amplification circuit, which mimics the signal amplification functionality. For example, the output signal from the hardware amplification circuit 805 may be A/D converted into a digital signal. The hardware amplification circuit 805 may have a gain $G_{plant}$.

The waveform signal 801 may be a trapezoidal waveform. The waveform signal 801 may be acquired from the initial signal acquisition module 210. In some embodiments, the waveform signal 801 may be generated by the waveform generator. In some embodiments, the waveform signal 801 may be stored in the storage unit 506. The control sub-module 401 may retrieve the waveform signal 801 directly from the storage unit 506.

The feedforward controller 802 may perform feedforward control. The feedforward controller 802 may comprise one or more load models. The load models may comprise information related to parameters such as load impedance, and load inductance, etc. In some embodiments, the feedforward controller 802 may comprise inductive reactance information for the load inductance, denoted as "$L_S$", and the feedforward controller 802 may comprise load impedance information, denoted as "R". The feedforward controller may be a component of the feedforward control sub-unit 501-1.

The proportional controller 803 may perform proportional control, e.g. the scaling up of a signal, etc. In some embodiments, the output information from the proportional controller 803 is in proportional to the input information thereto. The proportional controller 803 may comprise one or more proportional coefficients, denoted as "$K_p$". The proportional controller 803 may be a component of the proportional integral (differential) control sub-unit 501-3.

The proportional controller 804 may perform integral control, e.g. the integration of a signal, etc. In some embodiments, the output information from the proportional controller 804 is in proportional to the integration of the input information thereto. The integral controller 804 may be a component of the proportional integral (differential) control sub-unit 501-3.

In some embodiments, the output signal from the hardware amplification circuit 805 may act as a feedback signal to the control sub-module 401, and the feedback signal may undergo a subtraction operation with the waveform signal 801, resulting in a difference signal. In some embodiments, the proportional controller 803 may scale up the difference signal, resulting in a proportional control signal; meanwhile, the integral controller 804 may calculate the integration of the difference signal, resulting in an integral control signal. In some embodiments, the proportional control signal and the integral control signal may be summed, resulting in a difference control signal. Meanwhile, the feedforward controller 802 may perform feedforward control on the waveform signal 801, resulting in a feedforward signal. The feedforward control signal may be summed with the difference control signal, resulting in a control signal. In some embodiments, the control signal may be amplified by the hardware amplification circuit 805, resulting in an output signal. The output signal may be output to the gradient coil 240. The hardware amplification circuit 805 may be a component of the amplification circuit sub-module 403. The hardware amplification circuit 805 may be a common component shared by the amplification circuit sub-module 403 and signal processing sub-module 404.

In some embodiments, the characteristic output may be retrieved from the control sub-module 401. The characteristic output may be representative of the difference (i.e. the above mentioned difference signal) between the output signal and the input signal of the gradient power amplifier debugging system 120. The characteristic output may comprise an integral output, a proportional output, and/or a differential output of the PI(D) controller. The integral output may refer to the above mentioned integral control signal, as shown in a broken line in FIG. 8. The retrieval of the integral control signal may be performed by the data retrieval unit 503. The retrieved data may be filtered by the low-pass filter 806. In some embodiments, the low-pass filter 806 may be a second order low-pass filter. In some embodiments, the cutoff frequency of the low-pass filter 806 may be a frequency which is less than half of the sampling frequency. In some embodiments, the low-pass filter 806 may be omitted, or be replaced by other filters, e.g., by a notch filter. In some embodiments, if the data in the waveform signal 801 is a current signal, the retrieved data may be an integral information 807 of the current, e.g., a voltage signal. In some embodiments, the retrieved data may be stored in the storage unit 506. In some embodiments, the above-mentioned proportional control signal may be retrieved so as to obtain a proportional output (not shown in FIG. 8). In some embodiments, a differential controller may be added at the input or output of the proportional controller 803 and/or integral controller 804. The differential controller may have a parallel coupling relationship with the proportional controller 803 and/or integral controller 804. The differential controller may calculate the differential of the above mentioned difference signal, resulting in the differential control signal. In some embodiments, the above-mentioned differential control signal may be retrieved so as to obtain a differential output (not shown in FIG. 8).

In some embodiments, the retrieved integral signal 807 (i.e. the integral output), proportional output, and/or differential output may be used by the load parameter identification unit 504, may be used to compute the load parameters (including the load inductance, the load impedance, etc.), and then to adjust the control parameters of the feedforward controller 802, the proportional controller 803, and/or the integral controller 804 according to the result of load parameter computation.

According to some embodiments of the present application, FIG. 9 shows an exemplary flow diagram for parameter self-tuning process of the gradient power amplifier debugging system 120. The parameter self-tuning process may comprise initializing the system 901, identifying the load impedance 903, identifying the load inductance 904, adjusting the close loop control parameters 905, and checking the result of parameter self-tuning 906.

In step 901, initialization setup may be performed on the related parameters in the control sub-module 401 of the gradient power amplification debugging system 120. The initialization setup may be performed on the other modules as well. In some embodiments, the related parameters may be set to one or more system default values. The way of acquiring the system default values may comprise instrument automatic acquisition and acquisition under human instruction. For example, the system default values may be acquired from the input/output module 130-3, acquired via the signals generated by the processing module 130-2, or be specified by the system, or any combination of the above. The acquired system default value may be used directly for initialization setup, or may be stored in the storage unit 506 for later use. The system default values are not limited by input ordering or storage ordering. In some embodiments, the initialized parameters may comprise the parameters in the feedforward controller 802, e.g. the load inductance, load impedance of the load models, etc. The initialized parameters may comprise parameters in the proportional controller 803, the integral controller 804, etc. e.g., the proportional coefficient, the integral coefficient, etc. The initialized parameters may further comprise parameters related to checking. In some embodiments, the initialization setup may be omitted, e.g., the feedforward controller 802, the proportional controller 803, and/or the integral controller 804 may read system default values directly out of the storage unit 506 when needed. As noted, the initialization step 901 may perform initialization setup once or more times; the step 901 may be performed during the process of MR device assembling, or may be performed during maintenance or debugging process of the MR device; step 901 may precede step 902, or may be performed by being interleaved at least in part in steps 903, 904, 905 and 906.

In step 903, the load impedance of the gradient power amplification debugging system 120 may be identified, and the feedforward controller 802 may be adjusted. In some embodiments, the hardware amplification circuit 805 may output two or more pulse signals, which may be of appropriate amplitude and duration. Two or more output pulse signals may comprise the same, partially same, or different amplitudes and/or durations. When the hardware amplification circuit 805 output the pulse signals, an integral control signal may be retrieved from the integral controller 804, resulting in the integral output. The load impedance may be identified based on the integral output. In some embodiments, the identified value of the load impedance may be stored in the storage unit 506, and may be further used for the adjustment to the feedforward controller 802. The detailed process may refer to FIG. 10-B along with the description thereof.

In step 904, the load inductance of the gradient power amplification debugging system 120 may be identified, and the feedforward controller 802 may be adjusted. Step 904 may be based on the identified value of the load impedance in step 903. In some embodiments, the parameters in the load models in the feedforward controller 802 may be adjusted based on the identified value of the load impedance in step 903, and then the load inductance is identified. In some embodiments, the hardware amplification circuit 805 may output at least one pulse signal. The pulse signal may comprise appropriate amplitude and duration. When the hardware amplification circuit 805 output the pulse signals, an integral control signal may be retrieved from the integral controller 804, resulting in the integral output. The load inductance may be identified based on the integral output. In some embodiments, the identified value of the system inductance may be stored in the storage unit 506, and may be further used for the adjustment to the feedforward controller 802. The detailed process may refer to FIG. 11-B along with the description thereof.

In step 905, the proportional integral control parameter in the gradient power amplification debugging system 120 may be adjusted. Step 905 may be based on the identified value of the load inductance in step 904. In some embodiments, the parameters in the load models in the feedforward controller 802 may be adjusted based on the identified value of the load impedance in step 904. In step 905, the proportional integral control parameter (e.g. a proportional coefficient, an integral coefficient, etc.) may be calculated based on the identified value of the load inductance. The result of the calculation may be stored in the storage unit 506. The control parameters in the proportional controller 803, and/or the integral controller 804, respectively, may be adjusted according to the result of the calculation. The detailed process may refer to FIG. 12-B along with the description thereof.

In step 906, the debugging result of the gradient power amplification debugging system 120 may be checked. In some embodiments, the hardware amplification circuit 805 may output at least one test pulse. The test pulse may comprise appropriate amplitude and/or duration. When the hardware amplification circuit 805 output the test pulse, an integral control signal may be retrieved from the integral controller 804, resulting in the integral output. In step 906, the integral output may be judged, so as to achieve the checking on the result of system debugging. In step 906, the checking result may be output. The detailed process may refer to FIG. 13-B along with the description thereof.

As noted, the above description of the parameter self-tuning process of the the gradient power amplifier debugging system 120 is merely a specific example, rather than the only viable embodiment. Apparently, when appreciating the basic principles of parameter self-tuning, those skilled may make various modification and changes to the specific embodiments and steps of the parameter self-tuning in terms of forms and details without departing from these principles, make some simple inference and substitution without creative work, and make some adjustment or combination to the ordering of the various sub-units, and/or processing steps, where these modification and changes are still within the scope of the present disclosure. For instance, step 901 may be interleaved, at least in part, in the process of steps 903, 904, 905 and 906. In some embodiments, one or more steps may be added to the process, or be removed therefrom. For example, step 906 may be omitted. As another example, at least another parameter identification process, or at least another parameter adjustment process may be added between steps 903, 904, 905 and/or 906. In some embodiments, steps 903, 904 and 905, individually, partially, or all may be repeated several times to improve precision of the parameters thus obtained. In some embodiments, steps 901, 903, 904, 905 and 906 may all be performed automatically or under human instruction.

According to some embodiments of the present application, FIG. 10-A shows a schematic diagram of the load impedance identification sub-unit 1003. In some embodiments, the load impedance identification sub-unit 1003 may have the same functionality and structure as the load impedance identification sub-unit 601. In some embodiments, the hardware amplification circuit 805 may output a first amplitude pulse signal 1001 and a second amplitude pulse signal 1002. The first amplitude pulse signal 1001 may comprise an amplitude $I_{R1}$. The second amplitude pulse signal 1002 may comprise an amplitude $I_{R2}$. When the hardware amplification circuit 805 output the pulse signal, the characteristic output may be retrieved. For example, the integral control signal may be retrieved from the integral controller 804, resulting in the integral output. The load impedance may be identified based on the characteristic output, resulting in the mismatched impedance value $\Delta R$, from which the load impedance is identified.

According to some embodiments of the present application, FIG. 10-B shows an exemplary flow diagram of load impedance identification. The load impedance identification may comprise outputting a pulse signal 1011, retrieving a characteristic output (e.g. an integral output) 1012, computing a mismatched impedance 1017, computing a load impedance identification value 1018, adjusting a parameter of the feedforward controller 1019, etc. The load impedance identification process involves signals and/or pulses which may comprise one or more characteristic parameters, e.g., signal strength (or amplitude), signal duration, signal rising time, etc. The signal strength (or amplitude) of the signal or pulse may be a function of signal time. In some embodiments, a signal and/or a pulse may be represented by one or more arrays, e.g., a 2D array which may be comprised of signal strength (or amplitude) and signal time.

In step 1011, the hardware amplification circuit 805 may output two or more pulse signals. In some embodiment, the two or more pulse signals may be mono-polarity pulses. The mono-polarity pulses may be a pulse of mono-polarity, e.g., a positive pulse, or a negative pulse. The two or more pulse signals may comprise different amplitudes. The two or more pulse signals may comprise amplitudes which are great enough (e.g., not lower than a certain threshold) such that the retrieved difference of integral output depends merely on the load impedance. The two or more mono-polarity pulses may have their amplitudes and amplitude durations may be kept within certain ranges so as to ensure the characteristic response time of the response signal output from a particular region in the system is long enough. In some embodiments, the particular region in the system may be any position in the loop where the proportional controller 803 and the integral controller 804 are located. The characteristic response time may be a time interval notion or a time set. In some embodiments, the characteristic response time may comprise a starting time and an ending time of the response signal characteristic region, and may further comprise any number of time instants located therebetween. In some embodiments, the characteristic response time may be the signal plateau time or signal steady state time. The amplitudes that meet the conditions may comprise $I_{R1}$ and $I_{R2}$. In some embodiments, the pulse signal of the amplitude $I_{R1}$ has a plateau time of $\{T_{R1}\}$; and the pulse signal of the amplitude $I_{R2}$ has a plateau time of $\{T_{R2}\}$. In some embodiments, one or more of the amplitudes and the characteristic response times thereof may be input to the storage unit 506 as system default values in the system initialization step 901, may be input to the control sub-module 401 directly via the input/output module 130-3 in step 1011, may be generated automatically according to some rules by the control sub-module 401, or a combination of the above. The amplitudes comprising $I_{R1}$ and $I_{R2}$ may be stored in the storage unit 506 in any of the steps in the parameter self-tuning process prior to step 1017.

In step 1012, one or more characteristic output (e.g., an integral output) generated in step 1011 may be retrieved. In some embodiments, the integral output may be retrieved from the output signal of the integral controller 804. The integral output may have correspondence with the mono-polarity pulse signal output in step 1011. For example, in regard to the two mono-polarity pulses with the amplitudes of $I_{R1}$ and $I_{R2}$, respectively, the corresponding integral output may be $\Delta U_I(I_{R1})$ and $\Delta U_I(I_{R2})$, respectively. In some embodiments, $\Delta U_I(I_{R1})$ may be an integral output of the pulse signal with the amplitude $I_{R1}$ in the characteristic response time $\{T_{R1}\}$; and $\Delta U_I(I_{R2})$ may be an integral output of the pulse signal with the amplitude $I_{R2}$ in the characteristic response time $\{T_{R2}\}$. The integral output may be stored directly in the storage unit 506, or may be stored in the storage unit 506 after being processed. For example, the integral output may be filtered by the low-pass filter 806, or may be processed by other circuit components accordingly.

In step 1017, the mismatched impedance value $\Delta R$ may be computed. The mismatched impedance value $\Delta R$ may refer to the difference between the load impedance in the load model in the feedforward controller 802 and the real impedance of the gradient coil 240. The computation of the mismatched impedance value $\Delta R$ may be based on the related data in steps 1011, 1012, etc. In some embodiments, the above mentioned data may be computed to obtain the mismatched impedance value $\Delta R$. The related data may comprise the amplitude (including $I_{R1}$ and $I_{R2}$) of the mono-polarity pulse signal output in step 1011 and the characteristic response time (including $\{TR_{R1}\}$ and $\{T_{R2}\}$), and the characteristic output (including $\Delta U_I(I_{R1})$ and $\Delta U_I(I_{R2})$) retrieved in step 1012. In some embodiments, since the amplitudes of the one or more output mono-polarity pulses are great enough (e.g., no less than a certain threshold), the performance difference of the steady states under different DC is merely related to the line impedance, and thus $\Delta R$ may be computed based on the difference in the steady state integral output as retrieved. The steady state integral output may comprise $\Delta U_I(I_{R1})'$ and $\Delta U_I(I_{R2})'$, which may be determined based on the integral output $\Delta U_I(I_{R1})$ and $\Delta U_I(I_{R2})$ within the characteristic response time $\{T_{R1}\}$ and $\{T_{R2}\}$. In some embodiments, $\Delta U_I(I_{R1})'$ and $\Delta U_I(I_{R2})'$ may be obtained from $\Delta U_I(I_{R1})$ and $\Delta U_I(I_{R2})$ directly without considering the specific $\{T_{R1}\}$ and $\{T_{R2}\}$. For example, an output of $\Delta U_I(I_{R1})$ or $\Delta U_I(I_{R2})$ at the current signal time instant may be obtained every certain time interval from the signal starting time, and the current output is taken as $\Delta U_I(I_{R1})'$ or $\Delta U_I(I_{R2})'$ when the output no longer changes or when its change is lower than one or more thresholds.

In some embodiments, $\Delta R$ may be computed according to eq. (1):

$$\begin{cases} \Delta U_I(I_{R1})' = \Delta U(I_{R1}) + \Delta R \cdot I_{R1} \\ \Delta U_I(I_{R2})' = \Delta U(I_{R2}) + \Delta R \cdot I_{R2} \end{cases}, \quad (1)$$

wherein $\Delta U(I_{R1})$ and $\Delta U(I_{R2})$ may be equivalent voltage drops to which the mono-polarity pulses of the amplitudes $I_{R1}$ and $I_{R2}$ correspond, as caused by factors other than line impedance. In some embodiments, $\Delta U(I_{R1})$ and $\Delta U(I_{R2})$ may involve the relationship as shown in eq. (2):

$$\Delta U(I_{R1}) \approx \Delta U(I_{R2}). \quad (2)$$

In some embodiments, $\Delta R$ may be computed according to eq. (3):

$$\Delta R \cong \frac{\Delta U_I(I_{R1})' - \Delta U_I(I_{R2})'}{I_{R1} - I_{R2}}. \quad (3)$$

In some embodiments, when the number of the mono-polarity pulses output in step 1011 is three or more, the relationship between the integral output and the pulse amplitude may be represented by eq. (4):

$$\begin{cases} \Delta U_I(I_{R1})' = \Delta U(I_{R1}) + \Delta R \cdot I_{R1} \\ \Delta U_I(I_{R2})' = \Delta U(I_{R2}) + \Delta R \cdot I_{R2} \\ \quad \cdots \\ \Delta U_I(I_{Ri})' = \Delta U(I_{Ri}) + \Delta R \cdot I_{Ri} \end{cases}, \quad (4)$$

wherein i may be any integer greater than 2; $\Delta U_I(I_{R1})', \Delta U_I(I_{R2})' \ldots \Delta U_I(I_{Ri})'$ may be the steady state integral outputs to which the mono-polarity pulses of the amplitudes $I_{R1}$, $I_{R2} \ldots$ and $I_{R1}$ correspond, respectively; and $\Delta U(I_{R1}), \Delta U(I_{R2}) \ldots \Delta U(I_{Ri})$ may be the equivalent voltage drops to which the mono-polarity pulses of the amplitudes $I_{R1}$, $I_{R2} \ldots$ and $I_{Ri}$ correspond, respectively, as caused by factors other than line impedance. In some embodiments, $\Delta U(I_{R1})$, $\Delta U(I_{R2}) \ldots \Delta U(I_{Ri})$ may involve the relationship as shown in eq. (5):

$$\Delta U(I_{R1}) \cong \Delta U(I_{R2}) \cong \ldots \cong \Delta U(I_{Ri}). \quad (5)$$

In some embodiments, AR may be computed according to eq. (6) via statistics approach:

$$\Delta R \cong \frac{i \cdot \sum [\Delta U_I(I_{Rn})' \cdot I_{Rn}] - \sum \Delta U_I(I_{Rn})' \cdot \sum I_{Rn}}{i \cdot \sum (I_{Rn})^2 - (\sum I_{Rn})^2}, \quad (6)$$

wherein n represents an integer between 1 and i. Of course, the mismatched impedance value ΔR may be obtained by means other than eq. (3) and eq. (6). Those skilled may devise similar ways, or make supplements or amendments to the above equations to obtain ΔR after understanding the substance of the present application. Optionally, the mismatched impedance value ΔR as obtained may be further processed; the processing may comprise further modification which may be automated or under human instruction, and may comprise corresponding processing by the other circuit components in the system. The mismatched impedance value ΔR with or without being processed may be stored in the storage unit 506, or may be used in step 1018 directly.

In step 1018, load impedance value $R_r$ may be computed. The computation of the load impedance value $R_r$ may be obtained based on the related data in step 901, and/or step 1017. In some embodiments, the system default value $R_0$ of the load impedance initialized in step 901 and the mismatched impedance value ΔR computed in step 1017 may be used to compute and obtain $R_r$. For example, $R_r$ may be computed according to eq. (7):

$$R_r = R_0 + \Delta R. \quad (7)$$

In some embodiments, $R_r$ may be obtained by those skilled in other similar ways or based on other equations after understanding the substance of the present application. Optionally, the load impedance value $R_r$ as computed may be further processed; the processing may comprise further modification which may be automated or under human instruction, and may comprise corresponding processing by the other circuit components in the system. The load impedance value $R_r$ with or without being processed may be stored in the storage unit 506, or may be used in step 1019 directly.

In step 1019, the parameters of the feedforward controller 802 may be adjusted. In some embodiments, the adjustment may be based on the load impedance value $R_r$ computed in step 1018. In some embodiments, one or more data may be read out from the storage unit 506, and the parameters of the feedforward controller 802 may be adjusted according to the data read out. In some embodiments, the feedforward controller 802 may read the parameter values out of the storage unit 506 directly, and the load impedance value $R_r$ computed in step 1018, when being stored in the storage unit 506, may overwrite the system default value initialized in step 901.

As noted, the above description of the load impedance identification process is merely specific examples, and shall not be taken as the only viable embodiment. Apparently, when appreciating the basic principles of load impedance identification, those skilled may make various modification and changes to the specific embodiments and steps of the load impedance identification in terms of forms and details without departing from these principles, make some simple inference and substitution without creative work, and make some adjustment or combination to the ordering of the various sub-units, and/or processing steps, where these modification and changes are still within the scope of the present disclosure. For instance, steps 1011 and 1012, steps 1012 and 1017, steps 1017 and 1018, steps 1018 and 1019 may be combined. In some embodiments, one or more steps may be added to the process, or be removed therefrom. For example, at least another impedance computation parameter identification process, or at least one parameter optimization or modification process, or at least one feedforward control parameter adjustment process may be added between steps 1012, 1014, 1017, 1018 and/or 1019. As another example, steps 1011-1019 may be repeated one or more times individually, in part, or wholly, to further improve the precision of load impedance identification.

According to some embodiments of the present application, FIG. 11-A shows a schematic diagram of the load inductance identification sub-unit 1103. In some embodiments, the load inductance identification sub-unit 1103 may have the same functionality and structure as the load inductance identification sub-unit 602. In some embodiments, the hardware amplification circuit 805 may output a third pulse signal 1101. The third amplitude pulse signal may comprise an amplitude $I_{L1}$, and a rising time $T_{ramp}$. When the hardware amplification circuit 805 output the pulse signals, an integral control signal may be retrieved from the integral controller 804, resulting in the integral output. The load inductance may be identified based on the integral output, resulting in the mismatched inductance value ΔL, from which the load inductance is identified.

According to some embodiments of the present application, FIG. 11-B shows an exemplary flow diagram of load inductance identification. The load inductance identification process may be based on the load impedance computed in step 1018 and the feedforward control parameter adjusted in step 1019. The load inductance identification process may comprise outputting a pulse signal 1111, retrieving a characteristic output (e.g. an integral output) 1112, computing a mismatched inductance 1115, computing a load inductance value 1116, and adjusting the feedforward control parameter 1117, etc. The load inductance identification process involves signals and/or pulses which may comprise one or more characteristic parameters, e.g., signal strength (or amplitude), signal duration, signal rising time, etc. The signal strength (or amplitude) of the signal or pulse may be a function of signal time. In some embodiments, a signal and/or a pulse may be represented by one or more arrays, e.g., a 2D array which may be comprised of signal strength (or amplitude) and signal time.

In step 1111, the hardware amplification circuit 805 may output a group of pulse signals. In some embodiments, the pulse signals may comprise at least one mono-polarity pulse. The mono-polarity pulse may ensure that the characteristic response time of the response time output in a particular region inside the system is long enough. In some embodiments, the particular region in the system may be any position in the loop where the proportional controller 803 and the integral controller 804 are located. The characteristic response time may be a time interval notion or a time set. In some embodiments, the characteristic response time may comprise a starting time and an ending time of the response signal characteristic region, and may further comprise any number of time instants located therebetween. In some embodiments, the characteristic response time may be the signal rising time. The peak current of the mono-polarity pulse meeting the condition may comprise $I_{L1}$. The mono-polarity pulse may comprise a characteristic response time $\{T_{L1}\}$. In some embodiments, the characteristic response time may be the signal rising time $T_{ramp}$. In some embodiments, $\{T_{L1}\}$ may be long enough (e.g., not lower than a certain threshold), such that the integral output over the signal rising time is only related to the mismatched inductance. The related parameters of one or more of the mono-polarity pulses may be input to the storage unit 506 as system default values in the system initialization step 901, may be input to the control sub-module 401 via the input/output module 130-3 in step 1111, may be generated automatically according to some rules by the control sub-module 401, or a combination of the above. The peak current may be stored in the storage unit 506 in any of the steps in the load inductance identification process prior to step 1115.

In step 1112, one or more characteristic output (e.g., an integral output) generated in step 1111 may be retrieved. In some embodiments, the integral output may be retrieved from the output signal of the integral controller 804. The integral output has a correspondence with the mono-polarity pulse output in step 1111, e.g., it may correspond to the mono-polarity pulse comprising the peak current of $I_{L1}$, with a corresponding integral output of $\Delta U_I(I_{L1})$. In some embodiments, $\Delta U_I(I_{L1})$ may be an integral output of the pulse signal comprising a peak current of $I_{L1}$, over the characteristic response time $\{T_{L1}\}$. The retrieved integral output may be stored directly in the storage unit 506, or may be stored in the storage unit 506 after being processed. For example, the integral output may be filtered by the low-pass filter 806, or may be processed by other circuit components accordingly.

In step 1115, the mismatched inductance value $\Delta L$ may be computed. The mismatched inductance value $\Delta L$ may refer to the difference between the load inductance in the load model in the feedforward controller 802 and the real inductance of the gradient coil 240. The computation of the mismatched inductance value $\Delta L$ may be based on the related data in steps 1111, 1112, etc. In some embodiments, the above mentioned data may be computed to obtain the mismatched inductance value $\Delta L$. The related data may comprise the peak current (including $I_{L1}$) of the mono-polarity pulse signal output in step 1111 and the characteristic response time (including $\{T_{L1}\}$), and the characteristic output (including $\Delta U_I(I_{L1})$) retrieved in step 1112. Since the rising time of the one or more output mono-polarity pulse signal is long enough (e.g., not less than a certain threshold), the integral output during the current rising time is only related to the mismatched load inductance $\Delta L$, such that $\Delta L$ may be computed and obtained based on the integral output during the current rising time, the peak current, and the current rising duration. The integral signal output $\Delta U_I(I_{L1})'$ during the current rising time may be the integral output of $\Delta U_I(I_{L1})$ during the period of $\{T_{L1}\}$.

In some embodiments, $\Delta L$ may be computed according to eq. (8):

$$\Delta U_I(I_{L1})' = \Delta L \cdot \frac{I_{L1}}{t_{L1}}, \qquad (8)$$

wherein, $t_{L1}$ may be the duration of $\{T_{L1}\}$. $t_{L1}$ may be computed and obtained based on the starting time and ending time of $\{T_{L1}\}$. In some embodiments, $\Delta L$ may be computed according to eq. (9):

$$\Delta L = \Delta U_I(I_{L1})' \cdot \frac{t_{L1}}{I_{L1}}. \qquad (9)$$

In some embodiments, when the number of the mono-polarity pulses output in step 1111 is two or more, the relationship between the integral output and the peak current as well as the current rising time may be represented by eq. (10):

$$\begin{cases} \Delta U_I(I_{L1})' = \Delta L \cdot \dfrac{I_{L1}}{t_{L1}} \\ \cdots \\ \Delta U_I(I_{Li})' = \Delta L \cdot \dfrac{I_{Li}}{t_{Li}} \end{cases}, \qquad (10)$$

wherein, i may be any integer greater than 1.

In some embodiments, $\Delta L$ may be computed according to eq.(11) via statistics approach:

$$\Delta L = \frac{1}{i} \cdot \sum \left[ \frac{\Delta U_I(I_{Ln})'}{t_{Ln}} \cdot I_{Ln} \right], \qquad (11)$$

wherein n represents an integer between 1 and i. In some embodiments, the mismatched inductance value $\Delta L$ may be obtained by means other than eq. (9) and eq. (11). Those skilled may devise similar ways, or make supplements or amendments to the above equations to obtain $\Delta L$ after understanding the substance of the present application. Optionally, the mismatched inductance value $\Delta L$ as obtained may be further processed; the processing may comprise further modification which may be automated or under human instruction, and may comprise corresponding processing by the other circuit components in the system. The mismatched inductance value $\Delta L$ with or without being processed may be stored in the storage unit 506, or may be used in step 1116 directly.

In step 1116, load inductance value $L_r$ may be computed. The computation of the load inductance value $L_r$ may be obtained based on the related data in step 901, and/or step 1115. In some embodiments, the system default value $L_0$ of the load impedance initialized in step 901 and the mismatched inductance value $\Delta L$ computed in step 1115 may be used to compute and obtain $L_r$. In some embodiments, $L_r$ may be computed according to eq. (12):

$$L_r = L_0 + \Delta L. \qquad (12)$$

In some embodiments, $L_r$ may be obtained by those skilled in other similar ways or based on other equations after understanding the substance of the present application. Optionally, the load inductance as obtained may be further processed; the processing may comprise further modification which may be automated or under human instruction, and may comprise corresponding processing by the other circuit components in the system. The load inductance value with or without being processed may be stored in the storage unit 506, or may be used in step 1117 directly.

In step 1117, the parameters of the feedforward controller 802 may be adjusted. In some embodiments, the adjustment may be based on the load inductance value computed in step 1116. In some embodiments, one or more data may be read out from the storage unit 506, and the parameters of the feedforward controller 802 may be adjusted according to the data read out. In some embodiments, the feedforward controller 802 may read parameters from the storage unit 506 when needed. The load inductance value computed in step 1116 may then overwrite the system default value initialized in step 901 when being stored in the storage unit 506.

As noted, the above description of the load inductance identification process is merely specific examples, and shall not be taken as the only viable embodiment. Apparently, when appreciating the basic principles of load inductance identification, those skilled may make various modification and changes to the specific embodiments and steps of the load inductance identification in terms of forms and details without departing from these principles, make some simple inference and substitution without creative work, and make some adjustment or combination to the ordering of the various sub-units, and/or processing steps, where these modification and changes are still within the scope of the present disclosure. For instance, steps 1111 and 1112, steps 1112 and 1115, steps 1115 and 1116, steps 1116 and 1117 may be combined. In some embodiments, one or more steps may be added to the process. For example, at least another inductance computation parameter identification process, or at least one parameter optimization or modification process, or at least one feedforward control parameter adjustment process may be added between steps 1112, 1115, 1116, and/or 1117. Steps 1111-1117 may be repeated one or more times individually, in part, or wholly, to further improve the precision of the parameters thus obtained.

According to some embodiments of the present application, FIG. 12-A shows a schematic diagram of the PI control parameter adjustment sub-unit 1203. In some embodiments, the PI control parameter adjustment sub-unit 1203 may have the same functionality and structure as PI(D) control parameter adjustment sub-unit 701. In some embodiments, the parameters of the proportional controller 803, and the integral controller 804 (e.g. a proportional coefficient, an integral coefficient, etc.) may be calculated based on the identified value of the load inductance in step 1116. In some embodiments, the proportional coefficient $K_p$, and the integral coefficient $K_i$ may be adjusted according to the result of the calculation.

According to some embodiments of the present application, FIG. 12-B shows an exemplary flow diagram of PI control parameter adjustment. The PI control parameter adjustment process may be based on the load inductance $L_r$ computed in step 1116. The PI control parameter adjustment process may comprise computing the PI control parameter 1211, and adjusting the PI control parameter 1212.

In step 1211, the PI control parameters may be computed and obtained. The PI control parameter may comprise the proportional coefficient $K_p$ of the proportional controller 803, and the integral coefficient $K_i$ of the integral controller 804. In step 901, the proportional coefficient $K_p$, and the integral coefficient $K_i$ may be initialized as system default values $K_{p\_0}$ and $K_{i\_0}$, respectively. The PI control parameters as computed and obtained may be denoted as the proportional coefficient $K_{p\_m}$ and the integral coefficient $K_{i\_m}$. In some embodiments, the open-loop gain $G_{loop}$ for PI control, the transfer function $G_{plant}$ of the hardware amplification circuit 805, and the load inductance L may involve a relationship as shown in eq. (13):

$$G_{loop} = \left(K_p + \frac{K_i}{s}\right)G_{plant} \approx \left(K_p + \frac{K_i}{s}\right) / sL, \qquad (13)$$

wherein s may be representative of a Laplacian operator for the Laplacian transformation.

In some embodiments, $K_p$ and $K_i$ may be represented by eq. (14) and eq. (15), respectively:

$$K_p = \alpha \cdot L, \qquad (14)$$

and $$K_i = \beta \cdot L, \qquad (15)$$

wherein $\alpha$ and $\beta$ may be constants. In some embodiments, $\alpha$ and $\beta$ may be representative of the characteristic parameters for close-loop control. In some embodiments, the values of the close-loop control characteristic parameters may have a relationship with the bandwidth of the gradient power amplification system. In some embodiments, one or more close-loop control characteristic parameters may be input to the storage unit 506 as system default values in the system initialization step 901, may be input to the control sub-module 401 directly via the input/output module 130-3 in step 1211, may be generated automatically according to some rules by the control sub-module 401, or a combination of the above.

In some embodiments, the computation of $K_{p\_m}$ and $K_{i\_m}$ may be based on the load inductance value $L_r$ computed in step 1116, as shown in eq. (16) and eq. (17):

$$K_{p\_m} = \alpha \cdot L_r, \qquad (16)$$

and $$K_{i\_m} = \beta \cdot L_r \qquad (17)$$

Notably, the computation of the PI control parameters is not limited to eq. (16) and eq. (17). Those skilled may devise similar ways, or make supplements or amendments to the above equations to obtain the PI control parameters after understanding the substance of the present application, or may replace the PI control unit with feedback control unit of other types, e.g., a PID control unit. Optionally, the close-loop control tuning parameters as obtained may be further processed; the processing may comprise further modification which may be automated or under human instruction, and may comprise corresponding processing by the other circuit components in the system. The PI control parameters with or without being processed may be stored in the storage unit 506, or may be used in step 1212 directly.

In step 1212, the proportional controller 803, and the integral controller 804 may be adjusted according to the PI control parameters computed in step 1211. In some embodiments, the close-loop control parameters may be retrieved from the storage unit 506 directly and may be applied to the adjustment to the proportional controller 803 and the integral controller 804. In some embodiments, the proportional controller 803 and the integral controller 804 may read data out of the storage unit 506 directly when needed, and the PI control parameters computed in step 1211, when being stored in the storage unit 506, may overwrite the system default value initialized in step 901.

According to some embodiments of the present application, FIG. 13-A shows a schematic diagram of the checking sub-module 1303. In some embodiments, the checking sub-unit 1303 may have the same functionality and structure as the checking sub-unit 703. The hardware amplification circuit 805 may output one or more test pulse signals 1301. The test pulse signals 1301 may be dual-polarity pulse signals. In some embodiments, the test pulse signal 1301 may comprise a positive amplitude $I_{test}$ and a negative amplitude $-I_{test}$. When the hardware amplification circuit 805 outputs the pulse signals, an integral control signal may be retrieved from the integral controller 804, resulting in the integral output. In some embodiments, the maximum ($U_f(I_{test})$_max), and/or the minimum ($U_f(I_{test})$_min) of the integral output may be retrieved and judged so as to obtain the result of checking.

According to some embodiments of the present application, FIG. 13-B shows an exemplary flow diagram of parameter self-tuning checking. The checking process may be performed after step 1212. The checking process may comprise outputting a test pulse signal 1311, retrieving a characteristic output 1312, checking the debugging result 1313, and output checking result 1314, etc. The checking process involves signals and/or pulses which may comprise one or more characteristic parameters, e.g., signal strength (or amplitude), signal duration, signal rising time, etc. The signal strength (or amplitude) of the signal or pulse may be a function of signal time. In some embodiments, a signal and/or a pulse may be represented by one or more arrays, e.g., a 2D array which may be comprised of signal strength (or amplitude) and signal time.

In step 1311, the hardware amplification circuit 805 may output a group of test pulse signals. In some embodiments, the test pulse signals may be mono-polarity pulses, dual-polarity pulse signals, etc. The test pulse signal may comprise the signal as shown in FIG. 13-A, which comprises the amplitudes $I_{test}$ and $-I_{test}$. The related parameters (e.g. the amplitudes, the duration, etc.) for the test pulse signal may be input to the storage unit 506 as system default values in the system initialization step 901, may be input to the control sub-module 401 directly via the input/output module 130-3 in step 1011, may be generated automatically according to some rules by the control sub-module 401, or a combination of the above.

In step 1312, one or more characteristic output (e.g., an integral output) generated in step 1311 may be retrieved. In some embodiments, the integral output may be retrieved from the output signal of the integral controller 804. The integral output may have correspondence with the test pulse signal output in step 1311. For example, a corresponding integral output for the test pulse signal $I_{test}$ may be $\Delta U_f(I_{test})$. In some embodiments, the retrieved integral output may be stored directly in the storage unit 506, or may be stored in the storage unit 506 after being processed. For example, the integral output may be filtered by the low-pass filter 806, or may be processed by other circuit components accordingly.

In step 1313, the characteristic output (e.g., an integral output) retrieved in step 1312 may be checked. In some embodiments, the maximum ($U_f(I_{test})$_max), and the minimum ($U_f(I_{test})$_min) of the integral output $\Delta U_f(I_{test})$ retrieved may be judged. It may be determined whether the parameter self-tuning has succeeded or not based on determining whether $U_f(I_{test})$_max and $U_f(I_{test})$_min meet their respective threshold conditions. In some embodiments, the integral output $\Delta U_f(I_{test})$ may be read from the storage unit 506, and the maximum ($U_f(I_{test})$_max, and the minimum ($U_f(I_{test})$_min) may be found by computation. The checking may be based on one or more thresholds. In some embodiments, the thresholds may comprise a maximum threshold and a minimum threshold; and the checking may pass when $U_f(I_{test})$_max is not higher than the maximum threshold, and/or when $U_f(I_{test})$_min is not lower than the minimum threshold. In some embodiments, the retrieval of the maximum $U_f(I_{test})$_max and the minimum $U_f(I_{test})$_min may be omitted. For instance, all the data in $\Delta U_f(I_{test})$ may be compared or computed with the thresholds; and when one or more data in $\Delta U_f(I_{test})$ are not higher than the maximum threshold and not lower than the minimum threshold, the checking may pass. In some embodiments, multiple integral outputs may be retrieved, and the check may not pass unless each of the integral outputs meets the threshold condition. The thresholds may be stored into the storage unit 506 as system default values in the system initialization step 901, may be input to the control sub-module 401 via the input/output module 130-3 in the current step, may be generated automatically according to some rules by the control sub-module 401, or a combination of the above. The thresholds may be stored in the storage unit 506 in any of the steps in the self-tuning process prior to step 1313.

Optionally, in step 1314, the checking result may be output. For example, a check pass signal may be output when the check has passed; or a check failure signal may be output when the check has failed. In some embodiments, the check result may be output via the input/output module 130-3. Based on the check result, the system may further perform the subsequent steps or do it under human instructions.

As noted, the above description of the checking process is merely specific examples, and shall not be taken as the only viable embodiment. Apparently, when appreciating the basic principles of checking, those skilled may make various modification and changes to the specific embodiments and steps of the parameter self-tuning in terms of forms and details without departing from these principles, make some simple inference and substitution without creative work, and make some adjustment or combination to the ordering of the various sub-units, and/or processing steps, where these modification and changes are still within the scope of the present disclosure. For example, step 1314 may be not be necessary. Steps 1311 and 1312, steps 1313 and 1314 may be merged. In some embodiments, one or more steps may be added to the process. For instance, after step 1314, if the check succeeds, the system operation interface may be initiated; of if the check fails, an automated or human instructed trouble shooting function or spare element replacement function may be added.

According to some embodiments of the present application, FIG. 14 shows a schematic diagram of another embodiment of the control sub-module 401. The control sub-module 401 may comprise an input waveform signal 1401. The waveform signal 1401 may be generated by the waveform generator. The waveform signal 1401 may be a combination of one or more of a sinusoidal wave, a functional signal, a pulse signal, a scanning signal, or a synthesized signal, etc. In some embodiments, the waveform signal 1401 may provide the gradient power amplifier with the known reference signal as needed, in order to test the parameters in the gradient power amplifier (e.g., the load parameters, the control parameters, etc.). The waveform signal 1401 may be generated by the system automatically, or may be generated according to the data input by the user via the input/output module 130-3. In some embodiments, the waveform signal 1401 may mimic the signal generated by the spectrum analyzer, which may be a digital signal. The waveform signal 1401 may be a combination of one or more of a triangle wave, a sawtooth wave, a sinusoidal wave, or a trapezoidal wave, etc. In some embodiments, the input signal to the control sub-module 401 may be a trapezoidal wave.

In some embodiments, the hardware amplification circuit 1405 may amplify the signal. The amplified signal may be a waveform signal 1401, or may be a waveform signal 1401 after being processed. The hardware amplification circuit 1405 may have a gain $G_{plant}$. In some embodiment, the hardware amplification circuit 1405 may comprise a combination of one or more of a signal modulation sub-module 402, an amplification circuit sub-module 403, and/or a signal processing sub-module 404, etc.

In some embodiments, the control sub-module 401 may comprise a feedforward controller 1402, a proportional controller 1403, an integration controller 1404, a low bandwidth low-pass filter 1408, and a high bandwidth low-pass filter 1409. The feedforward controller 1402, the proportional controller 1403, and the integral controller 1404 may comprise the same functionality and structure as the feedforward controller 802, the proportional controller 803, and the integral controller 804 in FIG. 8.

In some embodiments, the parameters of the feedforward controller 1402 may be generated by the system automatically, or may be set by the operator via the input/output module 130-3, etc. In some embodiments, the feedforward controller 1402 may comprise one or more load models, for adjusting the precision of the output signal from the hardware amplification circuit 1405. In some embodiments, the feedforward controller 1402 may be omitted, and an embodiment without a feedforward controller 1402 or with the feedforward controller 1402 as set in another position is still within the scope of the present application.

In some embodiments, the low bandwidth low-pass filter 1408, and the high bandwidth low-pass filter 1409 may perform filter processing on the signals. The input signals to the low bandwidth low-pass filter 1408, and to the high bandwidth low-pass filter 1409 may come from the waveform signal 1401, the output signal from the hardware amplification circuit 1405, and/or any of the above mentioned signals after being processed. In some embodiments, the input signals to the low bandwidth low-pass filter 1408, and to the high bandwidth low-pass filter 1409 may be a signal which is based on the difference between the output signal of the hardware amplification circuit 1405 and the waveform signal 1401. The coupling between the low bandwidth low-pass filter 1408, and the high bandwidth low-pass filter 1409 may comprise a combination of one or more of a serial coupling, a parallel coupling, or a hybrid coupling, etc. In some embodiments, the parameters in the low bandwidth low-pass filter 1408, and the high bandwidth low-pass filter 1409 may be generated by the system automatically, or may be set by the operator according to the specific requirement (e.g., the operator may empirically input the reference empirical parameters into the filter, and the filter performs signal filtering according to the established parameters), or may be automatically updated by the system according to the feedback of the result of computation or checking. The parameters of the filter may comprise one or more parameters from a central frequency, a cutoff frequency, a passband bandwidth, a ripple, etc. In some embodiments, the low bandwidth low-pass filter 1408 may comprise a relatively low cutoff frequency, while the high bandwidth low-pass filter 1409 may comprise a relatively high cutoff frequency. In some embodiments, the relatively low cutoff frequency may refer to a cutoff frequency of the low bandwidth low-pass filter 1408 being lower than a cutoff frequency of the high bandwidth low-pass filter 1409. In some embodiments, the relatively high cutoff frequency may refer to a cutoff frequency of the high bandwidth low-pass filter 1409 being higher than a cutoff frequency of the low bandwidth low-pass filter 1408. In some embodiments, the cutoff frequencies of the low bandwidth low-pass filter 1408, and/or the high bandwidth low-pass filter 1409 may be selected, modified, or adapted, etc., according to the operational condition, load parameters, debugging performance, etc., either manually or automatically. The low bandwidth low-pass filter 1408, and the high bandwidth low-pass filter 1409 may be switched under certain conditions. The switching may be implemented by a switch 1410.

In some embodiments, the low bandwidth low-pass filter 1408, and/or a high bandwidth low-pass filter 1409 may be located in an arbitrary position in the close-loop control, for example, in a transmission channel for the feedback signal of the hardware amplification circuit 1405, in the input channel of the hardware amplification circuit 1405, or in an output channel of the PI controller.

The switch 1410 may switch between the low bandwidth low-pass filter 1408 and the high bandwidth low-pass filter 1409 according to one or more rules. The switching may be performed by the system automatically, or by the operator manually. In some embodiments, the rules for switching may be based on the input or output signal of the feedforward controller 1402, the proportional controller 1403, the integral controller 1404, the hardware amplification circuit 1405, or the waveform signal 1401. For instance, when the load parameters in the feedforward controller 1402 is lower than a certain threshold, the switch 1410 may switch to the high bandwidth low-pass filter 1409 automatically, such that the high bandwidth low-pass filter 1409 may be coupled to the close-loop control circuit. As another example, when the load parameters in the feedforward controller 1402 is higher than the certain threshold, the switch 1410 may switch to the low bandwidth low-pass filter 1408 automatically, such that the low bandwidth low-pass filter 1408 may be coupled to the close-loop control circuit.

In some embodiments, the low bandwidth low-pass filter 1408, and the high bandwidth low-pass filter 1409 may be combined into a low-pass filter. This low-pass filter comprises at least two parameter configurations, e.g., a configuration of a lower cutoff frequency, or a configuration of a higher cutoff frequency. The two parameter configurations may be chosen and setup automatically or manually. In some embodiments, the switch 1410 may be omitted.

In some embodiments, the proportional controller 1403 may implement fast tracing response control (e.g., assuming the input current error signal being 1A, if the proportional controller 1403 has a proportional coefficient of 20, the control signal for correcting the current error may be modulated to 20V); and the integral controller 1404 may implement tracing test error, and may eliminate static error. In some embodiments, the current error signal may refer to a difference between the waveform signal 1401 and the output signal of the hardware amplification circuit 1405. In some embodiments, the proportional coefficient of the proportional controller 1403, and/or the integral coefficient of the integral controller 1404 may be adjusted according to the load parameters (e.g., the load impedance, the load inductance, etc.).

Similar to FIG. 8, in some embodiments, the characteristic output may be retrieved from the control sub-module 401. The characteristic output may be representative of the difference (i.e. the above mentioned current difference signal) between the output signal and the input signal of the gradient power amplifier debugging system 120. The characteristic output may comprise an integral output, a proportional output, and/or a differential output of the PI(D) controller. The integral output may refer to the integral control signal, as shown in the broken line in FIG. 14, which is retrieved from the integral controller 1404. In some embodiments, the integral output as retrieved may be further processed, e.g., may be filtered by the filter. In some embodiments, if the data in the waveform signal 1401 is a current signal, the integral output as retrieved may be an integral signal 1407 of the current error signal, e.g., a voltage signal. In some embodiments, the integral output may be stored in the storage unit 506. For instance, the integral output may be stored in one or more datasheets. In some embodiments, the integral output stored in the datasheets may be retrieved by the operator, or may be retrieved by the system automatically. The load impedance, the load inductance, the proportional coefficient, and the integral coefficient, etc., may also be stored in the datasheets. The datasheets may comprise the raw data, updated data, and data after some calculation for the parameters. The data in the datasheets may be used for further data processing. The data processing may be based on the computation of one or more functions (e.g., a combination of one or more of subtraction, summing, multiplication, division, logarithm, exponential, quadratic function, multivariate function, integration, differentiation, etc.). The integral output may be further used for the identification of the load impedance (see, FIG. 10), the identification of the load inductance (see, FIG. 11), the computation of the PI control parameters (see, FIG. 12), etc. In some instances, the proportional control signal may be retrieved from the proportional controller 1403 so as to obtain a proportional output (not shown in FIG. 14). In some embodiments, a differential controller may be added at the input or output of the proportional controller 1403 and/or integral controller 1404. The differential controller may have a parallel coupling relationship with the proportional controller 1403 and/or integral controller 1404. The differential controller may calculate the differential of the above mentioned current error signal, resulting in the differential control signal. In some embodiments, the above-mentioned differential control signal may be retrieved so as to obtain a differential output (not shown in FIG. 14).

In some embodiments, the retrieved integral signal 1407 (i.e. the integral output), proportional output, and/or differential output may be used by the load parameter identification unit 504, may be used to compute the load parameters (including the load inductance, the load impedance, etc.), and then to adjust the control parameters of the feedforward controller 1402, the proportional controller 1403, and/or the integral controller 1404 according to the result of load parameter computation; or may be used to switch between the low bandwidth low-pass filter 1408 and/or the high bandwidth low-pass filter 1409.

According to some embodiments of the present application, FIG. 15-A shows a schematic diagram of the load adaptation unit 1503. In some embodiments, the load adaptation sub-unit 1503 may have the same functionality and structure as the load adaptation sub-unit 702. In some embodiments, the low bandwidth low-pass filter 1408 and the high bandwidth low-pass filter 1409 may be chosen and/or switched according to the load inductance $L_r$ identified in step 1116.

According to some embodiments of the present application, FIG. 15-B shows an exemplary flow diagram of load adaptation. The load adaptation process may comprise initialization 1511, identifying the load impedance 1513, identifying the load inductance 1514, determining the threshold 1515, computing the PI control parameter under a state of low inductance value 1516, switching the filter 1517, computing the PI control parameter under a state of high inductance value 1518, and adjusting the PI control parameter 1519.

Steps 1511, 1513, and 1514 may be the same as steps 901, 903, and 904 in the carrying out thereof. Notably, in some embodiments, step 1511 may comprise initialization setup for the filter parameters (e.g., the cutoff frequency). For example, the filter may be initially setup as a low bandwidth low-pass filter 1408, or a high bandwidth low-pass filter 1409. In some embodiments, the cutoff frequency of the filter may be set as an initial cutoff frequency. In some embodiments, the initial cutoff frequency may be the same as the cutoff frequency of the low bandwidth low-pass filter 1408, or the cutoff frequency of the high bandwidth low-pass filter 1409. In some embodiments, the initial cutoff frequency may be a system default value, or set by the user via the input/output module 130-3.

In step 1515, the load inductance $L_r$ as identified may be determined. The determination may be based on one or more thresholds. When the threshold condition is met, the load may be regarded as being in the state of low inductance value, and the load adaptation process may go to step 1516; while the threshold condition is not met, the load may be regarded as being in the state of high inductance value, and the load adaptation process may go to step 1518. In some embodiments, the threshold may be one or more values from 100 µH~1000 µH, e.g., 600 µH. Notably, the above description of the range of the threshold is merely for the convenience of description, and shall be taken as an example, rather than any limitation on the present application. In some embodiments, the thresholds may be stored into the storage unit 506 as system default values in the system initialization step 1511, may be input to the control sub-module 401 directly via the input/output module 130-3 in the current step, may be generated automatically according to some rules by the control sub-module 401, or a combination of the above.

In step 1516, the PI control parameters under the state of low inductance value may be computed and obtained. The computation of the PI control parameter may be based on eq. (16) and eq. (17). Notably, the PI control parameter may be computed by using different coefficients under different load conditions. For example, under the state of low inductance load, coefficients $(\alpha_L, \beta_L)$ may be used for the computation, while under the state of high inductance load, coefficients $(\alpha_H, \beta_H)$ may be used. Wherein, $\alpha_L$, $\beta_L$, $\alpha_H$, and $\beta_H$ may be constants, $\alpha_L$ and $\alpha_H$ may be different; and $\beta_L$ and $\beta_H$ may also be different.

In step 1517, the operational status of the filter may be adjusted. The adjustment process of the operational status may comprise the switching of the low-pass filters coupled into the close-loop circuit. For example, the switching may be between the low bandwidth low-pass filter 1408 and the high bandwidth low-pass filter 1409. In some embodiments, if, in step 1511, the filter is initialized as the low bandwidth low-pass filter 1408, then in step 1517, the filter may be switched to the high bandwidth low-pass filter 1409. In some embodiments, the number of the low-pass filters may be three or more; and in step 1515, the determination may be based on two or more thresholds. For example, the low-pass filters may be adjusted based on the comparison of the load inductance $L_r$ against a threshold, or the determination whether the load inductance value $L_r$ is between two thresholds. In some embodiments, the adjustment of the low-pass filters may be performed according to the result of determination in step 1515 either automatically or under human instruction. In some embodiments, the parameters of the low-pass filters may be adjusted directly. For example, if, in step 1511, the parameter of the low-pass filter is set to a lower cutoff frequency, then in step 1517, it may be set to a higher cutoff frequency. The higher cutoff frequency and the lower cutoff frequency may be representative of a relatively high cutoff frequency and a relatively low cutoff frequency when the two cutoff frequencies are compared to each other. In some embodiments, if, in step 1511, the filter is initialized as the high bandwidth low-pass filter 1409, then step 1517 may be carried out when the determination condition in step 1515 is not met; for example, step 1517 may be performed prior to (or after) step 1518 so as to switch the filter to the low bandwidth low-pass filter 1408.

In step 1518, the PI control parameters under the state of high inductance value may be computed. The computation of the PI control parameter may be based on eq. (16) and eq. (17). Notably, the PI control parameter may be computed by using different coefficients under different load conditions. For example, under the state of high inductance value, the coefficients $(\alpha_H, \beta_H)$ may be adopted. Wherein, $\alpha_H$, and $\beta_H$ may be constants, $\alpha_L$ and $\alpha_H$ may be different; and $\beta_L$ and $\beta_H$ may also be different. Notably, the computation of the PI control parameters is not limited to eq. (16) and eq. (17). Those skilled may devise similar ways, or make supplements or amendments to the above equations to obtain the PI control parameters after understanding the substance of the present application. Optionally, the PI control parameters as obtained may be further processed; the processing may comprise further modification which may be automated or under human instruction, and may comprise corresponding processing by the other circuit components in the system. The PI control parameters with or without being processed may be stored in the storage unit 506, or may be used in step 1519 directly.

In step 1519, the proportional controller 1403, and the integral controller 1404 may be adjusted according to the PI control parameters computed in step 1516 or step 1518. The implementation thereof may be the same as step 1212.

It should be noted that the above description of load adaptation processes is only a concrete example and should not be considered the only viable implementation. Obviously, for professionals in the art, after understanding the basic principles of load adaptation, various modifications and changes in the form and details of the specific embodiments and steps of load adaptation may be made without departing from this principle, and a number of simple deductions or substitutions may be made without any cost. Under the premise of creative labor, some adjustments or combinations are made to the sequence of steps, but these modifications and changes are still within the scope described above. For example, step 1517 can be executed without satisfying the threshold condition in step 1515. For example, step 1517 can be performed before step 1516, before (or after) step 1518, or after step 1519. Again, after step 1519, you can add a verification step.

According to some embodiments of the present application, FIG. 16 shows a schematic diagram of an embodiment of the gradient power amplifier debugging system 120. FIG. 16 may be a schematic diagram of the topology of the gradient power amplifier debugging system 120 and the control block diagram thereof. The gradient power amplifier debugging system 120 may comprise a feedforward controller 1602, a digital low-pass filter 1603, a PI controller 1604, a delay unit 1605, a modulator 1606, an amplification circuit 1608, an output filter 1609, and a gradient filter 1610. The gradient power amplifier debugging system 120 may have an input signal 1601. The gradient power amplifier debugging system 120 may retrieve a feedback signal 1602. The input signal 1602, and the feedback signal 1602 undergo the process of controlling and amplifying, and a signal is then output to the gradient coil 1611. In order to improve the quality of the output signal, the gradient power amplifier debugging system 120 may perform parameter self-tuning on the feedforward controller 1602, the digital low-pass filter 1603, the PI controller 1604, etc.

The input signal 1601 may be similar to the waveform signal 801 in FIG. 8, or the waveform signal 1401 in FIG. 14. The input signal 1601 may be acquired by the initial signal acquisition module 210.

The feedforward controller 1602 may be similar to the feedforward controller 802 in FIG. 8, or the feedforward controller 1402 in FIG. 14. The PI controller 1604 may comprise a proportional controller, and an integral controller. The proportional controller may be similar to the proportional controller 803 in FIG. 8, or the proportional controller 1403 in FIG. 14. The integral controller may be similar to the integral controller 804 in FIG. 8, or the integral controller 1404 in FIG. 14. The low-pass filter 1603 may comprise a low bandwidth low-pass filter and/or a high bandwidth low-pass filter. The low bandwidth low-pass filter may be similar to the low bandwidth low-pass filter 1408 in FIG. 14. The high bandwidth low-pass filter may be similar to the high bandwidth low-pass filter 1409 in FIG. 14. In some embodiments, the low-pass filter 1603 may be switched among the two or more low-pass filters. The feedforward controller 1602, the low-pass filter 1603, and the PI controller 1604 may be a component in the control sub-module 401.

In some embodiments, if the sampling rate of the low-pass filter 1603 is the same as that of the PI controller 1604, the low-pass filter 1603 may be coupled prior to, or after the PI controller 1604. In some embodiments, if the sampling rate of the low-pass filter 1603 is lower than that of the PI controller 1604, the low-pass filter 1603 may be coupled after the PI controller 1604. In some embodiments, if the sampling rate of the low-pass filter 1603 is higher than that of the PI controller 1604, the low-pass filter 1603 may be coupled prior to the PI controller 1604.

The signal delay 1605 may be representative of the signal delay in the system. The signal delay may refer to the delay in the output signal of the low-pass filter 1603, or the PI parameter controller 1604, etc., or that in the above mentioned signals after being processed. In some embodiments, the signal delay is system inherent. In some embodiments, one or more approaches may be utilized to reduce signal delay. For instance, the zero frequency of the PI controller 1604 may be adjusted (see FIG. 21) to obtain a phase compensation, in order to alleviate the control signal delay.

The modulator 1606 may modulate the signal. The signal modulation may comprise amplitude modulation, frequency modulation, phase modulation, pulse modulation, pulse density modulation, etc. The pulse modulation may be a combination of one or more of pulse width modulation (PWM), SPWM, PFM, and/or PCM. In some embodiments, the modulator 1606 may receive a phase compensation parameter (e.g., the PI parameter $K_i$ and $K_p$) for the delay unit 1605, and may adjust the PWM modulation parameter (e.g., phase shift), in order to achieve the phase compensation. The modulator 1606 may output one or more modulated signals. In some embodiments, the modulated signals 1607-1 to 1607-$n$ may be sent to the amplification circuits 1608-1 to 1608-$n$, so as to adjust the power adjustment function of the amplification circuits 1608-1 to 1608-$n$. The modulated signals 1607-1 to 1607-$n$ may correspond to the amplification circuits 1608-1 to 1608-$n$, respectively. For example, the modulated signal 1607-1 (i.e., PWM 1) may be sent to the amplification circuit 1608-1; and the modulated signal

1607-*n* (i.e., PWM n) may be sent to the amplification circuit 1608-*n*. The modulated signals 1607-1 to 1607-*n* may control the turning on and turning off of the switches in the corresponding H bridge, so as for the corresponding output ports to obtain a series signals of certain characteristics, which signals will replace the signals prior to modulation. By modulating the width of the pulses via the modulator 1606, the change of the output voltage and the output frequency may be achieved for the amplification circuits 1608-1 to 1608-*n*. The modulator 1606 may be set in the gradient power amplification debugging system 120 at where the pulse modulation is needed. The modulator 1606 may be a component of the signal modulation sub-module 402. In some embodiments, the modulator 1606 may be set in the amplification circuits 1608-1 to 1608-*n*.

The amplification circuits 1608-1 to 1608-*n* may provide power adjustment function for the gradient power amplifier debugging system 120. The amplification circuit may adjust the power of the input signal to the gradient power amplifier debugging system 120. The amplification circuit may comprise one or more power switch devices. The power switch devices may be Metal-Oxide-Semiconductor Field-Effect Transistors (MOSFET) or Insulated Gate Bipolar Transistors (IGBT). The power switch devices may make corresponding adjustment (e.g., a combination of one or more of scaling up, scaling down, switching, etc.) to the power of the input signal according to certain coupling rules, so as to achieve established goal of power output. The coupling rules may be a combination of one or more of parallel coupling, serial coupling, serial-parallel hybrid coupling, etc. In some embodiments, the amplification circuit 1608-*x* (1≤x≤n) may be an IGBT module; the coupling of 1608-1 to 1608-*n* may be a multi-stage interleaved concatenation of n H bridges formed by n IGBT modules in serial or in parallel. In the multi-stage interleaved concatenation of n H bridges of the amplification circuits 1608-1 to 1608-*n*, the equivalent switching frequency may be 2n times of that of a single transistor. By the design of the amplification circuit, the output current ripple may be effectively reduced, and the control bandwidth may be increased, while achieving high power output, so as to produce steadier high power output. The power adjustment component formed by the amplification circuits 1608-1 and 1608-*n* may be a component in the amplification circuit sub-module 403.

In some embodiments, the gradient power amplifier debugging system 120 may provide voltages $V_{dc-1}, \ldots, V_{dc-x}, \ldots, V_{dc-n}$ to the amplification circuits 1608-1 to 1608-*n*, respectively. The voltages $V_{dc-1}, \ldots, V_{dc-x}, \ldots, V_{dc-n}$ may come from external grid, or may come from an internal power supply module of the gradient power amplification debugging system 120. In some embodiments, the voltages $V_{dc-1}, \ldots, V_{dc-x}, \ldots, V_{dc-n}$ may be DC voltages. The voltages $V_{dc-1}, \ldots, V_{dc-x}, \ldots, V_{dc-n}$ may be the same, partially same, or different. In some embodiments, the voltages $V_{dc-1}, \ldots, V_{dc-x}, \ldots, V_{dc-n}$ may come from one or more voltage signals. The voltage signal may be a combination of one or more of a sinusoidal wave, a functional signal, a pulse signal, and a random signal, etc. In some embodiments, the voltages $V_{dc-1}, \ldots, V_{dc-x}, \ldots, V_{dc-n}$ may be independent from each other. In some embodiments, the voltages $V_{dc-1}, \ldots, V_{dc-x}, \ldots, V_{dc-n}$ may be a pulse signal, and by external grid input, the voltage amplitude may be in the range between ±10V.

The output filter 1609 may filter out the corresponding frequency components in the chopped wave of the high voltage output. For example, the output filter 1609 may comprise one or more capacitors $C_f$, one or more resistors $R_d$, and/or one or more inductors $L_f$. The coupling of the resistors $R_d$, capacitors $C_f$ and/or inductors $L_f$ may be a combination of one or more of a serial coupling, a parallel coupling, or a hybrid coupling. According to the difference in the processed signal, the output filter 1609 may be an analogous filter and/or a digital filter. According to the difference in the signal band as processed, the output filter 1609 may be a combination of one or more of a low-pass filter (which allows the signal components in the low band to pass), a highpass filter (which allows the signal components in the high band to pass), a bandpass filter (which allows the signals in a certain band to pass), and a bandstop filter (which allows the signals outside a certain band to pass). In some embodiments, the modulated signals 1607-1 to 1607-*n*, when amplified by the amplification circuits 1608-1 to 1608-*n*, may achieve high voltage output, so as to form a signal of the output voltage $V_o$. The output filter 1609 may filter out the high frequency chopped wave components of the output voltage signal. The output filter 1609 may be a component of the signal processing sub-module 404.

The gradient filter 1610 may filter out electromagnetic noise. In some embodiments, the MR imaging scanner 110 and the system console 130 may be installed in a device room and a scan room, respectively, while the gradient filter 1610 may be installed on the wall between the device room and the scan room. The gradient filter 1610 may block the electromagnetic noise in the device room and the scan room. In some embodiments, the gradient filter 1610 may be set between the inductance coil 1611 and the output filter 1609, so as to filter out electromagnetic interfering noise. The gradient filter 1610 may comprise one or more filters; and the coupling of the filters may be a combination of one or more of serial coupling, parallel coupling, or hybrid coupling. In some embodiments, the gradient filter 1610 may be a component of the signal processing sub-module 404. In some embodiments, the gradient filter 1610 may be a component outside the gradient power amplifier debugging system 120.

The gradient coil 1611 may be similar to the gradient coil 240 in FIG. 2. The gradient coil 1611 may receive the current signal output from the gradient power amplifier debugging system 120, to produce a corresponding gradient magnetic field. The gradient coil 1611 may be taken as a load of the gradient power amplifier debugging system 120. The gradient coil 1611 may involve one or more parameters, including the coil inductance $L_{coil}$ and the coil resistance r, etc. In some embodiments, the high voltage output $V_o$ produced by the amplification circuits 1608-1 to 1608-*n* may undergo the output filter 1609, and/or be filtered by the gradient filter 1610 to obtain a smooth voltage, which is applied to the gradient coil 1611 so as to obtain a smooth gradient current.

In order to improve the quality of the current signal received by the gradient coil 1611, the gradient power amplifier debugging system 120 may perform parameter self-tuning on the feedforward controller 1602, the digital low-pass filter 1603, the PI controller 1604, etc. In some embodiments, after appropriate parameter self-tuning, the gradient power amplifier debugging system 120 may output a current signal of higher precision; alternatively, the gradient power amplifier debugging system 120 may adapt to a load inductance in a broader range. In some embodiments, the input current to the gradient filter 1610 is the output current from the gradient power amplifier, which may be sampled as a feedback signal 1612. The feedback signal 1612 is subtracted from the input signal 1610, resulting in a difference signal. The difference signal goes into the low-pass filter unit 1603 for filtering process, and then goes into the PI controller 1604 for proportional integral control operation, resulting in a proportional integral control signal. Meanwhile, the feedforward controller 1602 may perform control operation on the input signal 1601, resulting in a feedforward control signal. The feedforward control signal may be summed with the proportional integral control signal, and then be processed by the delay unit 1605, the modulator 1606, the amplification circuits 1608-1 to 1608-$n$, and the output filter 1609, resulting in an output signal. Thus, a close-loop control is formed between the feedback signal 1612 and the input signal 1601. In the debugging process for the gradient power amplifier, a integral control signal may be be retrieved from the PI controller, resulting in an integral output. According to the integral output, a difference between the load impedance parameter in the feedforward controller 1602 and the coil resistor r of the gradient coil 1611, as well as a difference between the load inductance parameter of the feedforward controller 1602 and the inductance $L_{coil}$ of the gradient coil 1611 may be identified, and the load impedance parameter, the load inductance parameter in the feedforward controller 1602, the proportional coefficient and the integral coefficient in the PI controller 1604, and the filter parameters in the low-pass filter 1603 may be adjusted according to the differences. In some embodiments, the proportional coefficient and the integral coefficient in the PI controller 1604, and the filter parameters in the low-pass filter 1603 may be adjusted differently according to the different load inductance or load impedance as identified.

In some embodiments, the amplification circuits 1608-1 to 1608-$n$, the output filter 1609, and the gradient filter 1610 may be taken as one of the configurations of the hardware amplification circuit 1405 in FIG. 14. Any corresponding variant is within the scope of the present disclosure. In some embodiments, the feedforward controller 1602 may be omitted, and an embodiment without a feedforward controller 1602 or with the feedforward controller 1602 set in another position (e.g., coupled after the low-pass filter 1603) is still within the scope of the present application. In some embodiments, the low-pass filter 1603 may be located in an arbitrary position in the close-loop control, for example, in a transmission channel for the feedback signal 1612, in the input channel of the PI controller, in an input channel of the delay unit 1605, etc.

According to some embodiments of the present application, FIG. 17 shows a schematic diagram of the hardware structure of the gradient power amplifier debugging system 120. Such a hardware structure may be configured to implement the specific system as disclosed herein. The hardware structure may comprise a master computer 1701, a signal generator 1702, a control circuit 1703, an IGBT drive and the topological structure thereof 1704, a current sensor 1704, a gradient coil 1705, a communication port 1707, a CPU 1708, and/or a memory 1709.

The master computer 1701 may be a computer system which issues control instructions. The computer system may be a general purpose computer, or a specific purpose computer. In some embodiments, the master computer 1701 may conduct informational interaction with the control circuit 1703, and may supervise the operation state of the slave computers and/or provide real time feedback. The master computer 1701 may be coupled to the communication port 1707 in order to achieve data communication. The master computer 1701 may comprise a communication port 1707, a CPU unit 1708, and a memory 1709, etc. The central processing system (CPU) unit 1708, which comprises one or more processors, may be used to execute program commands.

The memory 1709 can be a different form of program storage unit and data storage unit, such as hard disk, read-only memory (ROM), random access memory (RAM), and so on. A computer-readable medium may take many forms, including but not limited to, tangible storage media, carrier media, or physical transmission media. Stable storage media may include: optical disks or disks, and other computer or similar devices used to implement the system components described in the diagram. Unstable storage media include dynamic memory, such as the main memory of the computer platform. The visible transmission media include coaxial cables, copper cables, and optical fibers, including the circuits that form the bus within the computer system. Carrier transmission media can transmit electrical, electromagnetic, acoustic or optical signals, which can be generated by radio frequency or infrared data communication methods. Common computer-readable media include hard disks, floppy disks, magnetic tapes, or any other magnetic medium; CD-ROM, DVD, DVD-ROM, or any other optical medium; punch cards, or any other physical storage medium containing a hole pattern; RAM, PROM, EPROM, FLASH-EPROM, or any other memory chip or tape; transfer of data or refers to A connection device for a carrier, cable, or transmission carrier, or any other program code and/or data that can be read by a computer. Many of these forms of computer-readable media can occur during the execution of instructions and the delivery of one or more results by the processor.

The signal generator 1702 may be an instrument producing a test signal. The signal source may be a combination of one or more of a sinusoidal wave, a functional signal, a pulse signal, a scanning signal, or a synthesized signal, etc. The signal generator 1702 may be used to provide the known reference signal as needed to the circuit under test, so as to test the other parameters in the circuit. In some embodiments, the signal generator 1702 may mimic the signal generated by the spectrum analyzer, which may be a digital signal.

The control circuit 1703 may be a control system which implements signal processing adjustment, pulse modulation (PWM) computation and/or informational interaction with the master computer 1701. The control circuit 1703 may implement the signal acquisition, processing, and generation of the control signal in the present application. The control circuit 1703 may comprise a master circuit and a supervision circuit. Wherein, the master circuit may comprise a data acquisition module (e.g., the initial signal acquisition module 210 in FIG. 2), a signal modulation module (e.g., the signal modulation sub-module 402 in FIG. 4), and a signal processing module (e.g., the signal processing sub-module 404 in FIG. 4). The data acquisition module, the signal modulation module, and the signal processing module may be similar to the corresponding description in FIGS. 2 and 4. The supervision circuit may achieve the communication and synchronization with the master computer. In some embodiments, the supervision circuit may control the chipset integration module so as to acquire and/or output an analogous signal and/or a digital signal via the input/output interface (GPIO interface).

The IGBT driving and topological structure thereof 1704 may be a circuit design of current adjustment. In some embodiments, the topological structure of IGBT may be a circuit design of current amplification. The circuit design may be an H bridge (full bridge) interleaved design.

The current sensor 1705 may transform, according to certain rules, the detected information (e.g. the current) into a signal that conforms to some standard. The current sensor 1705 may be one or more of a shunter, an electromagnetic current mutual inductor and a electronic current mutual inductor, a fibre current sensor, etc. In some embodiments, the current sensor 1705 may be coupled between the gradient coil 1706 and the control circuit 1703, and transform the high current feedback by the gradient coil to a current signal in a range acceptable to the control circuit. The gradient coil 1706 may be a magnetic field generation apparatus, which may generate a magnetic field as needed by the system by using the amplified current as received.

EMBODIMENTS

The following embodiments are exemplified merely for description convenience, rather than for limiting the present application to the exemplified embodiments.

Embodiment 1

According to some embodiments of the present application, FIG. 18 illustrates the a frequency response of the output voltage vs. the input current, when the gradient power amplifier is coupled to gradient coils of different inductance. As can be seen in the gain chart, resonance peak and notch are presented in both the high inductance and low inductance situations. The resonance peak may be a resonance which comes from the output filter; the notch may be a resonance which comes from the capacitance of the gradient filter and inductance of the gradient coil. As can be seen in the figure, as the inductance of the gradient coil increases, in the band region lower than the frequency where the resonance peak is located, the response of the output current to the input voltage decreases sharply; while at the frequency where the resonance peak is, the gain increases nevertheless. This may due to the fact that the resonance frequency of the output filter depends on the components thereof, and thus is nearly invariable; while the notch decreases when the capacitance of the gradient filter resonant with a greater inductance of the gradient coil, such that the notch moves further away from the resonance peak, thus weakening the mutual inhibition between the resonance peak and the notch. As can be seen in combination with the phase chart, in the band region lower than the notch frequency, the phase characteristics of the high inductance and the low inductance are substantively the same.

Embodiment 2

According to some embodiments of the present application, FIG. 19-A is a schematic diagram of the open-loop frequency response of the system along with the corresponding low-pass filter characteristics thereof, when the gradient power amplifier is coupled to the gradient coil of low inductance. According to some embodiments of the present application, FIG. 19-B is a schematic diagram of the open-loop frequency response of the system along with the corresponding low-pass filter characteristics thereof, when the gradient power amplifier is coupled to the gradient coil of high inductance while the system adopts the control parameters which correspond to the gradient coil of low inductance. As can be seen in FIG. 19-A, in the open-loop situation, the crossover frequency of the open-loop transfer function approximates the control bandwidth. In the event of a gradient coil of low inductance (e.g., 400 μH), the bandwidth may be as much as $7f_1$; accordingly, in the event of a gradient coil of high inductance (e.g., 900 μH), if the control parameters corresponding to the low inductance is maintained, the bandwidth thereof is reduced to $4f_1$ (as shown in FIG. 19-B), and the amplitude margin corresponding to the resonance peak becomes lower, as shown in FIG. 19-A. At that time, the signal amplification capability of the gradient amplifier does not meet the requirement of imaging. As can be seen, if the same control parameters are used for both high and low inductance gradient coils, the stability of the signal amplification is not guaranteed.

According to some embodiments of the present application, FIG. 19-C illustrates the open-loop frequency response that corresponds to the direct increase of the PI parameters, when the gradient power amplifier is coupled to the gradient coil of high inductance. As can be seen in the figure, increasing the PI parameters may avoid or reduce the phenomena of control bandwidth decreasing for high inductance as shown in FIG. 19-B. This approach may increase the bandwidth to $7f_1$, and the amplitude-frequency gain in the band region lower than the resonance frequency thereof may increase; however, in the meanwhile, the gain at the resonance peak rises to 0 dB or higher, and the corresponding phase crosses 180°. At this point, the control system has lost its stability. As can be seen, by increasing the PI parameters directly, the gain at the resonance peak rises as the bandwidth increases, and the stability of signal amplification is not guaranteed.

Embodiment 3

According to some embodiments of the present application, FIG. 20 illustrates the schematic diagram of the open-loop frequency response that corresponds to the increase of the PI parameters while adjusting the cutoff frequency of the low-pass filter, when the gradient power amplifier is coupled to the gradient coil of high inductance. As shown, by increasing the PI parameters, the bandwidth thereof may rise to $7f_1$; while the cutoff frequency of the low-pass filter is reduced to a frequency lower than that of the resonance peak, such that the resonance peak is significantly rejected. As can be seen, when the gradient coil is of high inductance, the PI parameters may be adjusted to increase bandwidth; the cutoff frequency of the low-pass filter may be adjusted to reject the resonance frequency, such that the stability of signal amplification is guaranteed. However, when switching to a lower cutoff frequency, there will be more phase lag. In order to ensure proper stability margin (including amplitude stability margin and/or phase stability margin, etc.) under desirable control bandwidth, for a gradient coil of high inductance, the zero frequency of the PI controller may be adjusted to obtain phase compensation.

Embodiment 4

According to some embodiments of the present application, FIG. 21 illustrates the phase characteristics of the PI controller and the low-pass filter at similar bandwidths, when the gradient power amplifier is coupled to gradient coils of different inductances. As shown in FIG. 21, in regard to a gradient coil of low inductance, the phase lag caused by the low-pass filter is $\varphi_1$; and the phase lag caused by the PI controller is $\varphi_2$. In regard to a gradient coil of high inductance, the phase lag caused by the low-pass filter is $\varphi_3$; and the phase lag caused by the PI controller is $\varphi_4$. When the sum of $\varphi_1$ and $\varphi_2$ is approximately same as the sum of $\varphi_3$ and $\varphi_4$, the corresponding phase margins of the two inductances may be substantively the same.

The basic concepts have been described above, and it is clear to those skilled in the art that the disclosure of the invention described above is merely an example and does not constitute a limitation on this application. Although it is not explicitly stated here, various modifications, improvements and amendments to this application may be made by those skilled in the art. Such modifications, improvements and amendments are recommended in this application, so they are still within the spirit and scope of the exemplary embodiments of this application.

At the same time, this application uses specific words to describe the implementation of this application. Such as "one embodiment", "one embodiment", and/or "some embodiments" means a feature, structure, or feature associated with at least one embodiment of the present application. It should therefore be emphasized and noted that two or more references to "one embodiment" or "one embodiment" or "one alternative embodiment" in different locations in this specification do not necessarily refer to the same embodiment. In addition, certain features, structures or features in one or more embodiments of the present application may be appropriately combined.

In addition, it will be understood by those skilled in the art that various aspects of the application may be described and described through a number of patentable categories or circumstances, including any new and useful process, machine, product or material combination, or any new and useful improvement to them. Accordingly, all aspects of this application may be executed entirely by hardware, entirely by software (including firmware, resident software, microcode, etc.), or by a combination of hardware and software. The above hardware or software can be referred to as "data block", "module", "sub-module", "engine", "unit", "sub-unit", "component" or "system". In addition, various aspects of this application may appear as computer products located in one or more computer-readable media, including computer-readable program coding.

A computer-readable signal medium may contain a propagating data signal encoding a computer program, such as on a baseband or as part of a carrier. The propagation signal may have many forms, including electromagnetic form, optical form, etc., or suitable combination form. A computer-readable signal medium may be any computer-readable medium other than a computer-readable storage medium that can communicate, propagate, or transmit programs for use by connecting to an instruction execution system, device, or device. Program encoding on a computer-readable signal medium can be propagated through any suitable medium, including radio, cable, fiber optic cable, radio frequency signal, or similar medium, or any combination of the above medium.

The computer program codes required for various parts of this application can be written in any one or more programming languages, including object-oriented programming languages such as Java, Scala, Smalltalk, Eiffel, JADE, Emerald, C++, C #, VB.NET, Python, and conventional programming languages such as C, Visual Basic, Fortran 2003. Perl, COBOL 2002, PHP, ABAP, dynamic programming languages such as Python, Ruby and Groovy, or other programming languages. The program code can be run entirely on a user computer, or as a separate software package on a user computer, or partially on a user computer, partially on a remote computer, or entirely on a remote computer or server. In the latter case, a remote computer can be connected to a user's computer in any form of network, such as a local area network (LAN) or a wide area network (WAN), or to an external computer (e.g. via the Internet), or in a cloud computing environment, or as a service, such as software as a service (SaaS).

In addition, unless explicitly stated in the claim, the order of processing elements and sequences, the use of digital letters, or the use of other names described herein are not intended to limit the order of the application process and method. Although some of the invention embodiments currently considered useful are discussed by various examples in the above disclosure, it should be understood that such details serve only illustrative purposes and that additional claims are not limited to the disclosed embodiments, but rather are intended to cover all amendments that are consistent with the substance and scope of the embodiments of this application. Positive and equivalent combinations. For example, although the system components described above can be implemented by hardware devices, they can also be implemented only by software solutions, such as installing the described system on an existing server or mobile device.

Similarly, it should be noted that, in order to simplify the presentation of the disclosure of this application and thereby facilitate understanding of one or more embodiments of the invention, the foregoing description of the embodiments of this application sometimes incorporates multiple features into one embodiment, drawings or descriptions thereof. However, this disclosure method does not mean that the applicant needs more features than those mentioned in the claims. In fact, the characteristics of the embodiment are less than all the characteristics of the individual embodiments disclosed above.

Numbers describing the number of components and attributes are used in some embodiments, and it should be understood that such numbers for the description of embodiments are modified with modifiers "approximate", "approximate" or "substantially" in some examples. Unless otherwise stated, "approximate", "approximate" or "substantially" indicate that the number permits a variation of +20%. Accordingly, in some embodiments, the numerical parameters used in the specification and the claim are approximate values that can be changed according to the characteristics required by individual embodiments. In some embodiments, the numerical parameters should take into account the specified effective digits and adopt a general digit retention method. Although some embodiments of the present application are used to confirm numerical domains and parameter approximations of their range, in specific embodiments such values are set as precisely as possible within a feasible range.

For each patent, patent application, patent application publication and other materials cited in this application, such as articles, books, instructions, publications, documents, etc., the full contents of which are hereby incorporated into this application for reference. Except for the application history documents which are inconsistent with or conflict with the contents of this application, the documents which are the most widely limited to the claims of this application (currently or subsequently appended to this application) are also excluded. It should be noted that if the description, definition, and/or use of terms in the appendix to this application is inconsistent or inconsistent with the content described herein, the description, definition and/or use of terms in this application shall prevail.

Finally, it should be understood that the embodiments described in this application are intended only to illustrate the principles of the embodiments in this application. Other deformations may also fall within the scope of this application. Accordingly, alternative configurations of the embodiments of the present application may be regarded as consistent with the teaching of the present application as examples rather than limitations. Accordingly, the implementation of this application is not limited to the implementation examples clearly described and described in this application.

What is claimed is:

1. A control method for debugging a gradient power amplifier for driving a gradient coil of a magnetic resonance system, the gradient power amplifier comprising a control unit, which comprises: a close-loop control sub-unit configured to produce a characteristic output based on an input signal and an output signal of the gradient power amplifier; and a feedforward control sub-unit including a load model with load parameters related to the gradient coil, the method comprising:

initializing parameters of the close-loop control sub-unit and the feedforward control sub-unit with default values, wherein the load parameters are initialized to default load parameters;

retrieving a characteristic output of the close-loop sub unit, the characteristic output representing differences between the default load parameters and real load parameters;

computing the real load parameters according to the characteristic output of the close-loop sub unit; and adjusting the parameters of the close-loop sub-unit and feedforward sub-unit according to the real load parameters.

2. A gradient power amplifier, comprising:

a control unit, comprising a close-loop control sub-unit and a feedforward control sub-unit;

an initialization unit configured to initialize the control unit with default parameters, wherein the default parameters comprises default load parameter;

a data retrieval unit configured to retrieve a characteristic output of the close-loop control sub-unit, the characteristic output representing differences between the default load parameters and real load parameters;

a load parameter identification unit, configured to compute the real load parameters according to the characteristic output; and a control parameter adjustment unit, configured to adjust the one or more control parameters of the control unit according to the computed real load parameter.

3. A magnetic resonance system comprising:

a gradient coil configured to generate a gradient magnetic field;

a gradient power amplifier configured to drive the gradient coil;

a processor comprising:

a close-loop control sub-unit configured to produce a characteristic output based on an input signal and an output signal of the gradient power amplifier;

a feedforward control sub-unit including a load model with load parameters related to the gradient coil; and a storage unit configured to store executable instructions which, when executed by the processor, causes the processor to implement:

retrieving a characteristic output of the close-loop control sub-unit, the characteristic output represents differences of between the default load parameters and the real load parameters;

computing the real load parameters according to the characteristic output of the close-loop control sub-unit; and adjusting one or more control parameters of the control unit according to the real load parameter.

4. The method of claim 1, wherein
the close-loop control sub-unit comprises at least a proportional integral (PI) controller or a proportional integral differential (PID) controller.

5. The method of claim 4, wherein the characteristic output comprises at least an integral output of the close-loop control sub-unit.

6. The method of claim 1, wherein the load model comprises at least a load inductance L and/or a load resistance R, and the difference between the default load parameters and real load parameters comprises:

a difference resistance $\Delta R$ between a default load resistance R of the load model and a real load resistance R'; and/or a difference inductance $\Delta L$ between a default load inductance L of the load model and a real load inductance L'.

7. The method of claim 6, wherein retrieving the characteristic output comprises:

retrieving a first characteristic output of the close-loop control unit when the gradient power amplifier outputs a pulse signal of a first amplitude; and retrieving a second characteristic output of the close-loop control unit when the gradient power amplifier outputs a pulse signal of a second amplitude;

the first amplitude and the second amplitude are not lower than a first threshold, and the first threshold may be such that a difference between the first characteristic output and the second characteristic output is only dependent on the load resistance parameter R of the load model.

8. The method of claim 7, wherein the load resistance parameter is obtained by the following method:

computing a difference resistance $\Delta R$ between the default load resistance parameter R of the load model and the real load resistance R', according to the first characteristic output and the second characteristic output; and adjusting the load resistance of the load model to $\Delta R+R$, according to the difference resistance $\Delta R$ and the default load resistance R of the load model.

9. The method of claim 6, wherein retrieving the characteristic output further comprises:

retrieving a third characteristic output of the closed-loop control unit when the gradient power amplifier outputs a pulse signal of a third amplitude, wherein the pulse signal of the third amplitude comprises a rising time of $T_{ramp}$, and the rising time $T_{ramp}$ is not lower than a second threshold, such that a characteristic output in the rising time $T_{ramp}$ is only dependent on the load inductance L of the load model.

10. The method of claim 9, wherein the load parameter comprises the load inductance, and the load inductance is obtained by the following method:

computing a difference inductance $\Delta L$ between the default load inductance L of the load model and the real load inductance L', according to the third characteristic output and the rising time $T_{ramp}$; and adjusting the load inductance of the load model to $\Delta L+L$, according to the difference inductance $\Delta L$ and the default load inductance L of the load model.

11. The method of claim 6, wherein the close-loop control sub-unit comprises at least a proportional integral (PI) controller, the parameters of the closed-loop control sub-unit comprises control parameters, and the control parameters comprise a proportional coefficient $K_p$ and an integral coefficient $K_i$ of a PI controller.

12. The method of claim 11, wherein adjusting the control parameters of the closed-loop control sub unit comprises adjusting a value of the proportional coefficient $K_p$ to $\alpha L$, wherein $\alpha$ is a constant.

13. The method of claim 11, wherein adjusting the control parameters of the closed-loop control sub unit further comprises adjusting a value of the integral coefficient $K_i$ to $\beta L'$, wherein $\beta$ is a constant.

14. The method of claim 4, wherein the close-loop control sub-unit further comprises a first digital low-pass filter.

15. The method of claim 11, wherein adjusting the control parameters of the closed-loop control sub unit comprises:
comparing the real load inductance L' to a threshold;
adjusting the proportional coefficient $K_p$ to $\alpha_1 L'$ and the integral coefficient $K_i$ to $\beta_1 L'$, if the real load inductance L' is lower than the threshold, wherein $\alpha_1$ is a constant, and $\beta_1$ is a constant; and
adjusting the proportional coefficient $K_p$ to $\alpha_2 L'$ and the integral coefficient $K_i$ to $\beta_2 L'$, if the real load inductance L' is higher than the threshold, wherein $\alpha_2$ is a constant, and $\beta_2$ is a constant.

16. The method of claim 15, wherein the initializing comprises initializing a cutoff frequency of the first digital low-pass filter to an initial cutoff frequency.

17. The method of claim 16, wherein adjusting the parameters of the close-loop control sub-unit comprises:
comparing the real load inductance L' to a threshold;
adjusting the cutoff frequency of the first digital low-pass filter to a first cutoff frequency, if the real load inductance L' is lower than the threshold; and
adjusting the cutoff frequency of the first digital low-pass filter to a second cutoff frequency, if the real load inductance L' is higher than the threshold.

18. The method of claim 17, wherein the first cutoff frequency or the second cutoff frequency equals to the initial cutoff frequency.

19. The method of claim 11, wherein the close-loop control sub-unit comprises a second and a third digital low-pass filter with their specific cutoff frequency, and adjusting the control parameters of the control unit comprises:
comparing the real load inductance L' to a threshold; and
switching between the second digital low-pass filter and the third digital low-pass filter according to the result of the comparison.

20. The system of claim 3, further comprising a first digital low-pass filter and a second digital low-pass filter, wherein when executed by the processor, the executable instructions further cause the processor to implement:
comparing the real load parameter to a threshold; and
switching between the first digital low-pass filter and the second digital low-pass filter based on a result of the comparison.

* * * * *